US007119262B1

(12) United States Patent
Smith et al.

(10) Patent No.: US 7,119,262 B1
(45) Date of Patent: *Oct. 10, 2006

(54) PRODUCTION OF TRANSGENIC POINSETTIA

(75) Inventors: Franzine Smith, Geneva, NY (US); Tau-San Chou, Batavia, IL (US); Robert Eisenreich, North Aurora, IL (US); John Sanford, Geneva, NY (US); Alan Blowers, St. Charles, IL (US); Joyce Van Eck, Ithaca, NY (US)

(73) Assignee: Sanford Scientific, Inc., Waterloo, NY (US)

( * ) Notice: Subject to any disclaimer, the term of this patent is extended or adjusted under 35 U.S.C. 154(b) by 519 days.

This patent is subject to a terminal disclaimer.

(21) Appl. No.: 08/903,944

(22) Filed: Jul. 31, 1997

(51) Int. Cl.
*A01H 5/00* (2006.01)
*C12N 15/82* (2006.01)
*C12N 15/29* (2006.01)
*C12N 15/31* (2006.01)
*C12N 15/33* (2006.01)
*C12N 15/62* (2006.01)

(52) U.S. Cl. ............... 800/323; 800/278; 800/279; 800/283; 800/286; 800/288; 800/290; 800/302; 435/69.8; 435/200

(58) Field of Classification Search .............. 435/419, 435/430–1, 431, 470, 69.7, 69.8, 200; 800/205, 800/DIG. 67, 279, 283, 280, 287, 288, 290, 800/293, 300, 301, 302, 323
See application file for complete search history.

(56) References Cited

U.S. PATENT DOCUMENTS 5,945,579 A * 8/1999 Smith ..................... 800/298
6,235,973 B1 * 5/2001 Smith et al. ............. 800/279

FOREIGN PATENT DOCUMENTS

| WO | WO 90 10073 | 9/1990 |
| WO | WO 90 11770 | 10/1990 |
| WO | EP 0 472 987 | 3/1992 |
| WO | WO 95 01439 | 1/1995 |
| WO | WO 95 26634 | 10/1995 |
| WO | WO 96 11566 | 4/1996 |
| WO | WO 97 21815 | 6/1997 |

OTHER PUBLICATIONS

Nataraia et al. Morphogenesis in embryonal callus of *Euphorbia pulcherrima* in vitro. Current Science. 44(4):136-137, 1975.*
Preil. In vitro culture of poinsettia in the The Scientific Basis of Poinsettia Production, Stromme (ed.), pp. 49-56, The Agricultural University of Norway, 1994.*
Cheetham et al. Transformation of *Euphorbia lathyris* by *Agrobacterium rhizogenes*. Acta Horticulturae. 426:511-518, Aug. 1996.*
Xu et al. Plant Cell Reports 13:237-241, 1994.*
D'Halluin et al. Plant Cell 4:1495-1505, Dec. 1992.*
Caesar et al. Plant Disease 78(8):796-800, 1994.*
Oran, S. Pharmaceutical Biology 37(4):296-299, 1999.*
Litz, R. Journal of Plant Physiol. 132(2):190-193, 1988.*
Hartmann et al, eds, Plant Propagation: Principles and Practices, Fifth Edition, Prentice Hall: Englewood Cliffs, NJ, p. 500, 1990.*
Slightom et al. Embo J. 4(12):3069-3077, 1985.*
Sinkar et al. Genes & Development 2(6):688-697, 1988.*
Sukhapinda et al Plant Mol. Biol. 8:209-216, 1987.*
Visser et al. Theor. Appl. Genet. 78(4):594-600, 1989.*
Ooms et al. Theor. Appl. Genet. 71(2):325-329, 1985.*
Trulson et al. Theor. Appl. Genet. 73:11-15, 1986.*
David et al. Bio/Technology 2(1):73-76, Jan. 1984.*
Pythoud et al. Bio/Technology 5(12):1323-1327, Dec. 1987.*
Rech et al. Jour. Exp. Botany 39(206):1275-1285, Sep. 1988.*
Lelu et al. Plant Cell, Tissue & Organ Culture 36:117-127, 1994.*
DeWald et al. J. Amer. Soc. Hort. Sci. 114(5):837-841, 1989.*
Simone, G. Diseases of Poinsettia. In: APSNet. Common Names of Plant Diseases. (updated Nov. 2000).*
DeCleene et al. The Botanical Review 42(4): 389-466 (Oct.-Dec. 1976).*
Nataraja et al. In Vitro Production of Shoot Buds in *Euphorbia pulcherrima*; Current Science, vol. 42, No. 16, pp. 577-578, (1973).
Gupta Morphogenesis in Embryonal Callus of *Euphorbia pulcherrima* In Vitro; Current Science, vol. 44, No. 4, pp. 136-137 (1975).
Preil "In Vitro Culture of Poinsettia"; in The Scientific Basis of Poinsettia Production, Stromme (ed.) pp. 49-56 (The Agricultural University of Norway 1994).
Miki et al. "Procedures for Introducing Foreign DNA into Plants," in Methods in Plant Molecular Biology and Biotechnology, Glick et al. (eds.), pp. 67-88 (CRC Press 1993).
Christou "Application to Plants," in Particle Bombardment Technology for Gene Transfer, Yang et al. (eds.), pp. 71-99, (Oxford University Press 1994).
Lee et al. "Phytoplasma induced free-branching in commercial poinsettia cultivars," *Nature Biotechnology*, vol. 15, Feb. 1997, pp. 178-182.
Preil et al. "Somatic embryogenesis in bioreactor culture," *Acta Horticultura*, vol. 289, 1991, pp. 179-192.
Rosa-Marquez et al. "*In vitro* propagation of disease-free bromelia, poinsettia and dracaena in Puerto Rico," *Phytopathology*, vol. 81, No. 6, 1991, p. 699.
Follansbee et al. "Transformation of *Euphorbia lathyris* by Agrocacterium," *In vitro*, vol. 31, No. 3, 1995, p. 72A.

* cited by examiner

*Primary Examiner*—David T. Fox
(74) *Attorney, Agent, or Firm*—McDonnell Boehnen Hulbert & Berghoff LLP

(57) ABSTRACT

Since its introduction into North America over 170 years ago, the poinsettia has become a major ornamental potted plant, and is an important component of the U.S. floral industry. Susceptibility to insect pests and diseases caused by pathogens remains a problem for poinsettia production, even under greenhouse conditions. While chemical treatment can control certain insect pests and disease pathogens, such treatment can also have an adverse effect upon poinsettias. The methods described herein provide a means to genetically engineer transgenic poinsettia that express macromolecules capable of protecting the plant against the insects and pathogens. The production of transgenic plants can also be used to enhance the commercial value of poinsettia by controlling characteristics such as flower color.

26 Claims, 1 Drawing Sheet

```
                          SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
         (A) LENGTH: 23 amino acids
         (B) TYPE: amino acid
         (C) STRANDEDNESS: single
         (D) TOPOLOGY: linear (xi) SEQUENCE DESCRIPTION: SEQ ID NO:1:

Gly Ile Gly Lys Phe Leu His Ser Ala Lys Lys Phe Gly Lys Ala Phe
1               5                   10                  15

Val Gly Glu Ile Met Asn Ser
            20

(2) INFORMATION FOR SEQ ID NO:2:

(i) SEQUENCE CHARACTERISTICS:
         (A) LENGTH: 21 amino acids
         (B) TYPE: amino acid
         (C) STRANDEDNESS: single
         (D) TOPOLOGY: linear (xi) SEQUENCE DESCRIPTION: SEQ ID NO:2:

Gly Met Ala Ser Lys Ala Gly Ala Ile Ala Gly Lys Ile Ala Lys Val
1               5                   10                  15

Ala Leu Lys Ala Leu
            20

(2) INFORMATION FOR SEQ ID NO:3:

(i) SEQUENCE CHARACTERISTICS:
         (A) LENGTH: 22 amino acids
         (B) TYPE: amino acid
         (C) STRANDEDNESS: single
         (D) TOPOLOGY: linear (xi) SEQUENCE DESCRIPTION: SEQ ID NO:3:

Gly Ile Gly Lys Phe Leu Lys Ser Ala Lys Lys Phe Gly Lys Ala Phe
1               5                   10                  15
```

```
Val Lys Ile Leu Asn Ser
            20

(2) INFORMATION FOR SEQ ID NO:4:

(i) SEQUENCE CHARACTERISTICS:
        (A) LENGTH: 21 amino acids
        (B) TYPE: amino acid
        (C) STRANDEDNESS: single
        (D) TOPOLOGY: linear (xi) SEQUENCE DESCRIPTION: SEQ ID NO:4:

Lys Ile Ala Gly Lys Ile Ala Lys Ile Ala Gly Lys Ile Ala Lys Ile
1               5                  10                  15

Ala Gly Lys Ile Ala
            20

(2) INFORMATION FOR SEQ ID NO:5:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO:5:

Lys Arg Lys Arg Ala Val Lys Arg Val Gly Arg Leu Lys Lys Leu
1               5                  10                  15

Ala Arg Lys Ile Ala Arg Leu Gly Val Ala Phe
            20                  25

(2) INFORMATION FOR SEQ ID NO:6:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..72

(ix) FEATURE:
        (A) NAME/KEY: mat_peptide
        (B) LOCATION: 1..72

(xi) SEQUENCE DESCRIPTION: SEQ ID NO:6:

ATG GGC ATC GGA AAG TTC CTT CAC AGT GCA AAG AAG TTC GGA AAG GCC      48
Met Gly Ile Gly Lys Phe Leu His Ser Ala Lys Lys Phe Gly Lys Ala
1               5                  10                  15

TTC GTG GGT GAG ATC ATG AAC AGT TAA                                  75
Phe Val Gly Glu Ile Met Asn Ser
            20

(2) INFORMATION FOR SEQ ID NO:7:

(i) SEQUENCE CHARACTERISTICS:
        (A) LENGTH: 24 amino acids
        (B) TYPE: amino acid
        (D) TOPOLOGY: linear (ii) MOLECULE TYPE: protein (xi) SEQUENCE DESCRIPTION: SEQ ID NO:7:

Met Gly Ile Gly Lys Phe Leu His Ser Ala Lys Lys Phe Gly Lys Ala
1               5                  10                  15
```

Phe Val Gly Glu Ile Met Asn Ser
            20

(2) INFORMATION FOR SEQ ID NO:8:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..69

(ix) FEATURE:
        (A) NAME/KEY: mat_peptide
        (B) LOCATION: 1..69

(xi) SEQUENCE DESCRIPTION: SEQ ID NO:8:

```
ATG GGA ATC GGC AAG TTC CTC AAG AGC GCA AAG AAG TTT GGC AAG GCC      48
Met Gly Ile Gly Lys Phe Leu Lys Ser Ala Lys Lys Phe Gly Lys Ala
 1               5                  10                  15

TTC GTG AAG ATC CTG AAC TCC TAA                                      72
Phe Val Lys Ile Leu Asn Ser
            20
```

(2) INFORMATION FOR SEQ ID NO:9:

(i) SEQUENCE CHARACTERISTICS:
        (A) LENGTH: 23 amino acids
        (B) TYPE: amino acid
        (D) TOPOLOGY: linear (ii) MOLECULE TYPE: protein (xi) SEQUENCE DESCRIPTION: SEQ ID NO:9:

```
Met Gly Ile Gly Lys Phe Leu Lys Ser Ala Lys Lys Phe Gly Lys Ala
 1               5                  10                  15

Phe Val Lys Ile Leu Asn Ser
            20
```

(2) INFORMATION FOR SEQ ID NO:10:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..66

(ix) FEATURE:
        (A) NAME/KEY: mat_peptide
        (B) LOCATION: 1..66

(xi) SEQUENCE DESCRIPTION: SEQ ID NO:10:

```
ATG AAG ATC GCC GGA AAG ATA GCA AAG ATT GCG GGG AAA ATC GCG AAG      48
Met Lys Ile Ala Gly Lys Ile Ala Lys Ile Ala Gly Lys Ile Ala Lys
 1               5                  10                  15

ATC GCT GGC AAA ATC GCG TAA                                          69
Ile Ala Gly Lys Ile Ala
            20
```

(2) INFORMATION FOR SEQ ID NO:11:

(i) SEQUENCE CHARACTERISTICS:

(A) LENGTH: 22 amino acids
    (B) TYPE: amino acid
    (D) TOPOLOGY: linear (ii) MOLECULE TYPE: protein (xi) SEQUENCE DESCRIPTION: SEQ ID NO:11:

Met Lys Ile Ala Gly Lys Ile Ala Lys Ile Ala Gly Lys Ile Ala Lys
1               5                   10                  15

Ile Ala Gly Lys Ile Ala
            20

(2) INFORMATION FOR SEQ ID NO:12:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..81

(ix) FEATURE:
        (A) NAME/KEY: mat_peptide
        (B) LOCATION: 1..81

(xi) SEQUENCE DESCRIPTION: SEQ ID NO:12:

ATG AAG AGG AAG CGT GCA GTT AAG AGG GTG GGA CGT CGA TTG AAG CTT      48
Met Lys Arg Lys Arg Ala Val Lys Arg Val Gly Arg Arg Leu Lys Leu
1               5                   10                  15

GCA AGA AAG ATC GCA AGG CTC GGT GTG GCT TTC TAA                      84
Ala Arg Lys Ile Ala Arg Leu Gly Val Ala Phe
            20                  25

(2) INFORMATION FOR SEQ ID NO:13:

(i) SEQUENCE CHARACTERISTICS:
        (A) LENGTH: 27 amino acids
        (B) TYPE: amino acid
        (D) TOPOLOGY: linear (ii) MOLECULE TYPE: protein (xi) SEQUENCE DESCRIPTION: SEQ ID NO:13:

Met Lys Arg Lys Arg Ala Val Lys Arg Val Gly Arg Arg Leu Lys Leu
1               5                   10                  15

Ala Arg Lys Ile Ala Arg Leu Gly Val Ala Phe
            20                  25

(2) INFORMATION FOR SEQ ID NO:14:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..117

(ix) FEATURE:
        (A) NAME/KEY: mat_peptide
        (B) LOCATION: 1..117

(xi) SEQUENCE DESCRIPTION: SEQ ID NO:14:

ATG CTT CTC GCT ATT GCC TTC TTG GCA TCA GTT TGC GTG TCT TCC ATG      48

```
Met Leu Leu Ala Ile Ala Phe Leu Ala Ser Val Cys Val Ser Ser Met
 1               5                  10                  15
```

```
GGC ATC GGA AAG TTC CTT CAC AGT GCA AAG AAG TTC GGA AAG GCC TTC        96
Gly Ile Gly Lys Phe Leu His Ser Ala Lys Lys Phe Gly Lys Ala Phe
                20                  25                  30
```

```
GTG GGT GAG ATC ATG AAC AGT TAA                                       120
Val Gly Glu Ile Met Asn Ser
        35
```

(2) INFORMATION FOR SEQ ID NO:15:

(i) SEQUENCE CHARACTERISTICS:
        (A) LENGTH: 39 amino acids
        (B) TYPE: amino acid
        (D) TOPOLOGY: linear (ii) MOLECULE TYPE: protein (xi) SEQUENCE DESCRIPTION: SEQ ID NO:15:

```
Met Leu Leu Ala Ile Ala Phe Leu Ala Ser Val Cys Val Ser Ser Met
 1               5                  10                  15

Gly Ile Gly Lys Phe Leu His Ser Ala Lys Lys Phe Gly Lys Ala Phe
                20                  25                  30

Val Gly Glu Ile Met Asn Ser
        35
```

(2) INFORMATION FOR SEQ ID NO:16:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..108

(ix) FEATURE:
        (A) NAME/KEY: mat_peptide
        (B) LOCATION: 1..108

(xi) SEQUENCE DESCRIPTION: SEQ ID NO:16:

```
ATG CTT CTC GCT ATT GCC TTT TTG GCA TCA GTT TGC GTG TCT TCC GGA        48
Met Leu Leu Ala Ile Ala Phe Leu Ala Ser Val Cys Val Ser Ser Gly
 1               5                  10                  15

ATG GCC TCT AAG GCA GGT GCT ATC GCC GGC AAA ATC GCG AAG GTG GCA        96
Met Ala Ser Lys Ala Gly Ala Ile Ala Gly Lys Ile Ala Lys Val Ala
                20                  25                  30

TTG AAG GCC CTT TAA                                                   111
Leu Lys Ala Leu
        35
```

(2) INFORMATION FOR SEQ ID NO:17:

(i) SEQUENCE CHARACTERISTICS:
        (A) LENGTH: 36 amino acids
        (B) TYPE: amino acid
        (D) TOPOLOGY: linear (ii) MOLECULE TYPE: protein (xi) SEQUENCE DESCRIPTION: SEQ ID NO:17:

```
Met Leu Leu Ala Ile Ala Phe Leu Ala Ser Val Cys Val Ser Ser Gly
 1               5                  10                  15

Met Ala Ser Lys Ala Gly Ala Ile Ala Gly Lys Ile Ala Lys Val Ala
```

```
                    20                  25                  30
Leu Lys Ala Leu
        35

(2) INFORMATION FOR SEQ ID NO:18:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (ix) FEATURE:
         (A) NAME/KEY: CDS
         (B) LOCATION: 1..114

(ix) FEATURE:
         (A) NAME/KEY: mat_peptide
         (B) LOCATION: 1..114

(xi) SEQUENCE DESCRIPTION: SEQ ID NO:18:

ATG CTT CTC GCT ATT GCC TTC TTG GCA TCA GTT TGC GTG TCT TCC ATG           48
Met Leu Leu Ala Ile Ala Phe Leu Ala Ser Val Cys Val Ser Ser Met
 1               5                  10                  15

GGA ATC GGC AAG TTC CTC AAG AGC GCA AAG AAG TTT GGC AAG GCC TTC           96
Gly Ile Gly Lys Phe Leu Lys Ser Ala Lys Lys Phe Gly Lys Ala Phe
                20                  25                  30

GTG AAG ATC CTG AAC TCC TAA                                              117
Val Lys Ile Leu Asn Ser
        35

(2) INFORMATION FOR SEQ ID NO:19:

(i) SEQUENCE CHARACTERISTICS:
        (A) LENGTH: 38 amino acids
        (B) TYPE: amino acid
        (D) TOPOLOGY: linear (ii) MOLECULE TYPE: protein (xi) SEQUENCE DESCRIPTION: SEQ ID NO:19:

Met Leu Leu Ala Ile Ala Phe Leu Ala Ser Val Cys Val Ser Ser Met
 1               5                  10                  15

Gly Ile Gly Lys Phe Leu Lys Ser Ala Lys Lys Phe Gly Lys Ala Phe
                20                  25                  30

Val Lys Ile Leu Asn Ser
        35

(2) INFORMATION FOR SEQ ID NO:20:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (ix) FEATURE:
         (A) NAME/KEY: CDS
         (B) LOCATION: 1..108

(ix) FEATURE:
         (A) NAME/KEY: mat_peptide
         (B) LOCATION: 1..108

(xi) SEQUENCE DESCRIPTION: SEQ ID NO:20:

ATG CTT CTC GCT ATT GCC TTC TTG GCA TCA GTT TGC GTG TCT TCC AAG           48
Met Leu Leu Ala Ile Ala Phe Leu Ala Ser Val Cys Val Ser Ser Lys
 1               5                  10                  15
```

```
ATC GCC GGA AAG ATA GCA AAG ATT GCG GGG AAA ATC GCG AAG ATC GCT        96
Ile Ala Gly Lys Ile Ala Lys Ile Ala Gly Lys Ile Ala Lys Ile Ala
            20                  25                  30

GGC AAA ATC GCG TAA                                                   111
Gly Lys Ile Ala
        35

(2) INFORMATION FOR SEQ ID NO:21:

(i) SEQUENCE CHARACTERISTICS:
        (A) LENGTH: 36 amino acids
        (B) TYPE: amino acid
        (D) TOPOLOGY: linear (ii) MOLECULE TYPE: protein (xi) SEQUENCE DESCRIPTION: SEQ ID NO:21:

Met Leu Leu Ala Ile Ala Phe Leu Ala Ser Val Cys Val Ser Ser Lys
 1               5                  10                  15

Ile Ala Gly Lys Ile Ala Lys Ile Ala Gly Lys Ile Ala Lys Ile Ala
            20                  25                  30

Gly Lys Ile Ala
        35

(2) INFORMATION FOR SEQ ID NO:22:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..126

(ix) FEATURE:
        (A) NAME/KEY: mat_peptide
        (B) LOCATION: 1..126

(xi) SEQUENCE DESCRIPTION: SEQ ID NO:22:

ATG CTT CTC GCT ATT GCC TTC TTG GCA TCA GTT TGC GTG TCT TCC AAG        48
Met Leu Leu Ala Ile Ala Phe Leu Ala Ser Val Cys Val Ser Ser Lys
 1               5                  10                  15

AGG AAG CGT GCA GTT AAG AGG GTG GGA CGT CGA TTG AAG AAG CTT GCA        96
Arg Lys Arg Ala Val Lys Arg Val Gly Arg Arg Leu Lys Lys Leu Ala
            20                  25                  30

AGA AAG ATC GCA AGG CTC GGT GTG GCT TTC TAA                           129
Arg Lys Ile Ala Arg Leu Gly Val Ala Phe
        35                  40

(2) INFORMATION FOR SEQ ID NO:23:

(i) SEQUENCE CHARACTERISTICS:
        (A) LENGTH: 42 amino acids
        (B) TYPE: amino acid
        (D) TOPOLOGY: linear (ii) MOLECULE TYPE: protein (xi) SEQUENCE DESCRIPTION: SEQ ID NO:23:

Met Leu Leu Ala Ile Ala Phe Leu Ala Ser Val Cys Val Ser Ser Lys
 1               5                  10                  15

Arg Lys Arg Ala Val Lys Arg Val Gly Arg Arg Leu Lys Lys Leu Ala
            20                  25                  30
```

```
Arg Lys Ile Ala Arg Leu Gly Val Ala Phe
         35                  40
```

PRODUCTION OF TRANSGENIC POINSETTIA

BACKGROUND OF THE INVENTION

1. Field of the Invention

The present invention relates to methods for producing transgenic flowering plants. In particular, this invention is directed to methods for producing transgenic poinsettia. This invention also is directed to transgenic poinsettia that express at least one macromolecule that either confers resistance to an insect pest or to a disease-causing pathogen, or otherwise enhances the commercial value of the plant.

2. Background

The poinsettia, *Euphorbia pulcherrima* Willd., is a member of the family Euphorbiaceae. The genus *Euphorbia* contains 700 to 1000 species, and is characterized by a single female flower that lacks petals and typically lacks sepals. The female flower is surrounded by individual male flowers, and the entire flower is enclosed in a cup-shaped cyathium. The red, white, yellow or pink portion of the plant, popularly referred to as the "flower," consists of modified leaves or bracts.

Since its introduction over 170 years ago, the poinsettia has become the primary potted flowering plant produced and sold in North America. In 1996, for example, the USDA reported sales of poinsettia in the top 36 poinsettia production states of over 59 million pots, having a 214 million dollar wholesale value. Consequently, production of poinsettia potted plants is an important component of the U.S. floral industry.

Insect pests and diseases caused by pathogens can kill poinsettias even under greenhouse conditions. See, for example, Ecke, Jr., et al. (eds.), THE POINSETTIA MANUAL, 3$^{rd}$ Edition (Paul Ecke Publications 1990). Illustrative insect pests include whiteflies, mealybugs, thrips, aphids, and spider mites, which damage poinsettias by withdrawing plant fluids. Moreover, the larvae of fungus gnats and lepidopterous insects harm poinsettias by feeding on various plant structures.

Poinsettia are also susceptible to diseases caused by fungi and bacteria. Fungal infestation, such as *Rhizoctonia* root and stem rot or *Pythium* root and stem rot can cause a complete collapse of the poinsettia. While other fungal infections, such as poinsettia scab or *Corynespora* bract spot may not destroy the plant per se, the disfigurement ruins the commercial value of the infected plant. Similarly, certain bacteria, including *Erwinia chrysanthemi*, can kill an infected poinsettia plant, while others, such as *Xanthomonas campestris* pv. *poinsettiaecola*, destroy the plant's marketability.

Although chemical treatment can control certain of these insect pests and disease pathogens, such treatment can also have an adverse effect upon poinsettias. An alternative to chemical treatment is to genetically engineer transgenic poinsettia that express polypeptides capable of protecting the plant against the insects and pathogens. The production of transgenic plants can further be used to enhance the commercial value of poinsettia by controlling characteristics such as flower color, early flowering, day neutrality, free branching, dwarfness, fragrance, and superior post harvest and shipping qualities.

However, there has been no report to date on the successful production of transgenic poinsettia. Thus, a need still exists for a method to introduce foreign genes into poinsettia to enhance the survivability or commercial value of the plants.

SUMMARY OF THE INVENTION

Accordingly, it is an object of the present invention to provide methods for the regeneration of poinsettia in vitro. It is another object of the present invention to provide methods of producing transgenic poinsettia plants.

It is a further object of this invention to provide transgenic poinsettia that express macromolecules as protection against insect pests and disease-causing pathogens.

It is a further object of the present invention to provide methods of modifying plant habit.

Yet another object of the present invention is to provide poinsettia plants that exhibit increased resistance to ethylene.

These and other objects are achieved, in accordance with one embodiment of the present invention by the provision of a method for in vitro regeneration of poinsettia plants comprising the steps: (a) incubating poinsettia plant tissue explants capable of producing reddish epidermal callus on callus induction medium; (b) subculturing reddish epidermal callus to embryo induction medium comprising casein hydrolysate to form embryogenic callus; (c) culturing said embryogenic callus on developmental medium; (d) culturing said embryogenic callus on maturation medium; and (e) recovering poinsettia plants from said embryos.

In another embodiment of the present invention, a method for producing transgenic poinsettia plants is provided comprising the steps of: (a) incubating poinsettia plant tissue explants capable of producing reddish epidermal callus on callus induction medium; (b) subculturing reddish epidermal callus to embryo induction medium comprising casein hydrolysate to form embryogenic callus; (c) introducing an expression vector into said embryogenic callus to produce transformed embryogenic callus, wherein said expression vector comprises a selectable marker gene and a second foreign gene, or (c') introducing two expression vectors into said embryogenic callus to produce transformed embryogenic callus, wherein one of said expression vectors comprises a selectable marker gene, and wherein the second of said expression vectors comprises a second foreign gene, (d) culturing said transformed embryogenic callus on selection medium;

(e) culturing said transformed embryogenic callus containing developing embryos on developmental medium; (f) culturing said transgenic embryos on maturation medium; and (g) recovering transgenic poinsettia plants from said transgenic embryos.

In yet another embodiment of the present invention, a method for producing transgenic poinsettia plants is provided comprising the steps of: (a) incubating poinsettia plant tissue explants capable of producing reddish epidermal callus in callus induction medium; (b) culturing embryogenic callus produced on said callus induction medium in liquid embryo induction medium; (c) filtering the culture and incubating the filtrate in fresh liquid embryo induction medium; (d) filtering the culture and the filtrate on solid embryo development medium; (e) culturing produced embryos on said embryo development medium on maturation medium; (f) culturing said embryos on callus induction medium; (g) culturing epidermal callus produced on said callus induction medium on embryo induction medium to form embryogenic callus; (h) introducing an expression vector into said embryogenic callus to produce transformed embryogenic callus, wherein said expression vector comprises a selectable marker gene and a second foreign gene, or introducing two expression vectors into said embryogenic callus to produce transformed embryogenic callus, wherein one of said expression vectors comprises a selectable marker gene, and wherein the second of said expression vectors comprises a second foreign gene; (i) culturing said transformed embryogenic callus on selection medium; (j) culturing said transformed embryogenic callus containing embryos on developmental medium; (k) culturing said transformed embryos to maturation medium; and (l) recovering transgenic plants from said transgenic embryogenic callus. The expression vector may be introduced into embryogenic callus by any number of available methods including microparticle bombardment.

Another embodiment of the present invention provides a transgenic poinsettia plant comprising at least one expression vector, wherein said expression vector comprises at least one foreign gene, and wherein said transgenic poinsettia plant expresses said foreign gene. The expression vector may further comprise a promoter such as the Cauliflower Mosaic Virus (CaMV) 35S promoter, the enhanced 35S promoter, the UBQ3 promoter, the UBQ10 promoter, the UBQ11 promoter, the UBQ14 promoter, the TEFA 1 promoter, the rolC promoter, and the Commelina Yellow Mottle Virus promoter, and wherein the expression of said foreign gene is under the control of the promoter.

Another embodiment of the present invention provides a transgenic poinsettia plant wherein the expression of a foreign gene confers resistance to disease caused by a virus, bacterium, fungus or insect. The foreign gene may disrupt the function of the virus such as a gene for a viral coat protein, 2'–5' oligonucleotide synthetase, viral genome antisense RNA, or pokeweed antiviral protein. The foreign gene may be an insect resistance gene such as a gene encoding tryptophan decarboxylase, lectin, or *Bacillus thuringiensis* toxin. The foreign gene may encode a polypeptide such as chitinase, a β-1,3-glucanase, ribosome-inactivating protein, lytic peptide, and plant defensin for resistance to a fungal or bacterial pathogen.

Yet another embodiment of the present invention provides a transgenic poinsettia plant transformed with a foreign gene encoding a mutated ethylene receptor that confers ethylene resistance. The mutated ethylene receptor gene may be the *Arabidopsis* etr-1 gene or a tomato NR gene.

Another embodiment of the present invention provides a transgenic poinsettia plant transformed with a foreign gene encoding isopentenyl transferase under the control of a promoter of a senescence-associated gene such as the *Arabidopsis* SAG12 gene promoter.

An embodiment of the present invention is a transgenic poinsettia plant transformed with a foreign gene encoding a polypeptide having a MADS box domain such as the PLENA gene, the SQUAMOSA gene, the DEFICIENS A gene, the GLOBOSA gene, the APTELA1 gene, the APETALA3 gene, the AGAMOUS gene, the OsMADS24 gene, the OsMADS45 gene, and the OsMADS1 gene.

Yet another embodiment of the present invention provides a transgenic poinsettia plant transformed with a foreign gene wherein the foreign gene modifies plant habit. The foreign gene that modifies plant habit may be the OsMADS1 or phyA gene.

DETAILED DESCRIPTION

1. Definitions

Figure 1:
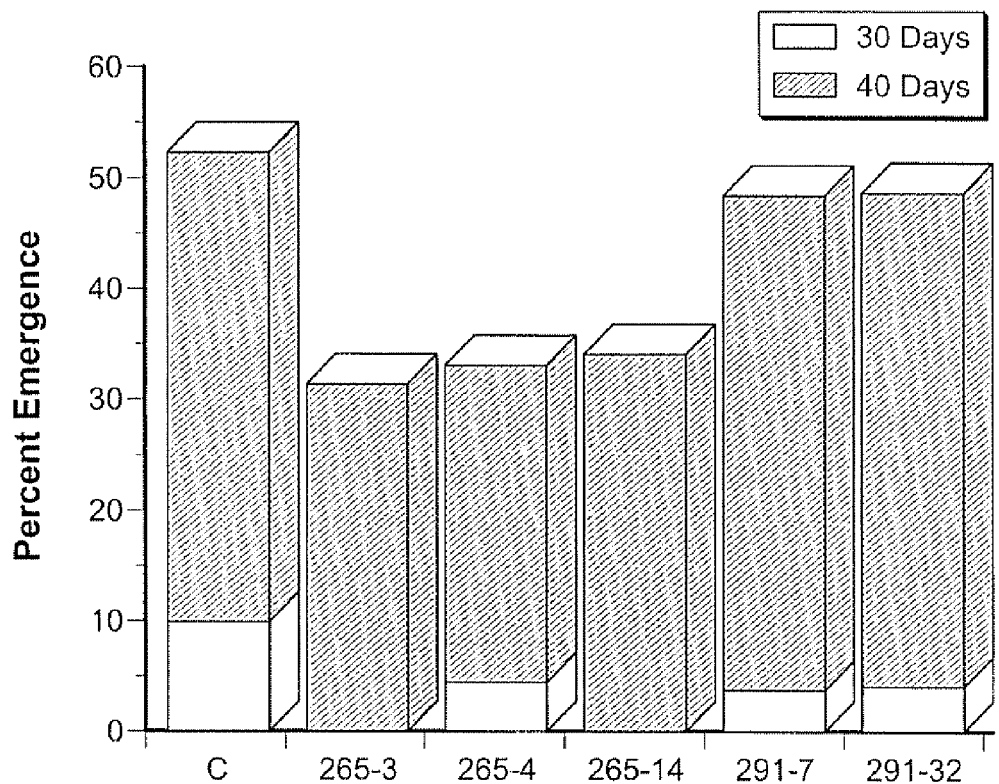
FIG. 1 illustrates the results of a study in which *Bemisia tabaci* were allowed to feed on tryptophan decarboxylase-expressing, tryptamine-accumulating transgenic poinsettia plants.

In the description that follows, a number of terms are used extensively. The following definitions are provided to facilitate understanding of the invention.

A structural gene is a DNA sequence that is transcribed into messenger RNA (mRNA) which is then translated into a sequence of amino acids characteristic of a specific polypeptide.

A promoter is a DNA sequence that directs the transcription of a structural gene. Typically, a promoter is located in the 5' region of a gene, proximal to the transcriptional start site of a structural gene. If a promoter is an inducible promoter, then the rate of transcription increases in response to an inducing agent. In contrast, the rate of transcription is not regulated by an inducing agent if the promoter is a constitutive promoter.

An isolated DNA molecule is a fragment of DNA that is not integrated in the genomic DNA of an organism. For example, a cloned *Bacillus thuringiensis* toxin gene is an illustration of an isolated DNA molecule. Another example of an isolated DNA molecule is a chemically-synthesized DNA molecule that is not integrated in the genomic DNA of an organism.

An enhancer is a DNA regulatory element that can increase the efficiency of transcription, regardless of the distance or orientation of the enhancer relative to the start site of transcription.

Complementary DNA (cDNA) is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand.

The term expression refers to the biosynthesis of a gene product. For example, in the case of a structural gene, expression involves transcription of the structural gene into mRNA and the translation of mRNA into one or more polypeptides.

A cloning vector is a DNA molecule, such as a plasmid, cosmid, or bacteriophage, that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance or ampicillin resistance.

An expression vector is a DNA molecule comprising a gene that is expressed in a host cell. Typically, gene expression is placed under the control of certain regulatory elements, including constitutive or inducible promoters, tissue-specific regulatory elements, and enhancers. Such a gene is said to be "operably linked to" the regulatory elements.

A foreign gene or a transgene refers in the present description to a DNA sequence that is operably linked to at least one heterologous regulatory element. For example, a cDNA molecule encoding an insect toxin is considered to be a foreign gene.

A recombinant host may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

A transgenic plant is a plant having one or more plant cells that contain an expression vector.

In eukaryotes, RNA polymerase II catalyzes the transcription of a structural gene to produce mRNA. A DNA molecule can be designed to contain an RNA polymerase II template in which the RNA transcript has a sequence that is complementary to that of a specific mRNA. The RNA transcript is termed an antisense RNA and a DNA sequence that encodes the antisense RNA is termed an antisense gene. Antisense RNA molecules are capable of binding to mRNA molecules, resulting in an inhibition of mRNA translation.

A ribozyme is an RNA molecule that contains a catalytic center. The term includes RNA enzymes, self-splicing RNAs, and self-cleaving RNAs. A DNA sequence that encodes a ribozyme is termed a ribozyme gene.

An external guide sequence is an RNA molecule that directs the endogenous ribozyme, RNase P, to a particular species of intracellular mRNA, resulting in the cleavage of the mRNA by RNase P. A DNA sequence that encodes an external guide sequence is termed an external guide sequence gene.

The term somatic embryo refers to tissue produced by proliferative embryogenic somatic cells which can germinate to form plants.

2. Overview

Although researchers have reported plant regeneration of poinsettia, none have indicated the successful production of transgenic cells or plants. See, for example, Nataraja et al., *Current Sci.* 42: 577 (1973); Gupta, *Current Sci.* 44: 136 (1975); Preil, "In Vitro Culture of Poinsettia," in THE SCIENTIFIC BASIS OF POINSETTIA PRODUCTION, Strømme (ed.), pages 49–56 (The Agricultural University of Norway 1994). However, the methods described herein provide a means to introduce foreign genes into poinsettia and recover transgenic plants. In addition, the procedures of the present application provide a tissue culture method that can be used for regeneration of various poinsettia cultivars. Such a general method is also not described in the prior art.

3. Methods for Producing Transgenic Poinsettia

The procedures described herein provide a means to produce transgenic poinsettia that contain an expression vector, and that express at least one foreign gene. The selection of an appropriate expression vector will depend upon the method of introducing the expression vector into host cells. Typically, an expression vector contains: (1) prokaryotic DNA elements coding for a bacterial replication origin and an antibiotic resistance marker to provide for the growth and selection of the expression vector in the bacterial host; (2) eukaryotic DNA elements that control initiation of transcription, such as a promoter; (3) DNA elements that control the processing of transcripts, such as a transcription termination/polyadenylation sequence; and (4) a foreign gene operably linked to the DNA elements that control transcription initiation. Optionally, an expression vector can also contain a selectable marker gene, as described below.

Expression vectors can be introduced into protoplasts, or into intact tissues or isolated cells. Preferably, expression vectors are introduced into callus cells. General methods of culturing plant cells and tissues are provided, for example, by Miki et al., "Procedures for Introducing Foreign DNA into Plants," in METHODS IN PLANT MOLECULAR BIOLOGY AND BIOTECHNOLOGY, Glick et al. (eds.), pages 67–88 (CRC Press, 1993), and by Dixon et al., PLANT CELL CULTURE: A PRACTICAL APPROACH, $2^{nd}$ Edition (IRL Press 1994).

Methods of introducing expression vectors into plant tissue include the direct infection or co-cultivation of plant tissue with *Agrobacterium tumefaciens*. Horsch et al., *Science* 227:1229 (1985). Descriptions of *Agrobacterium* vector systems and methods for *Agrobacterium*-mediated gene transfer are provided by Gruber et al., "Vectors for Plant Transformation," in METHODS IN PLANT MOLECULAR BIOLOGY AND BIOTECHNOLOGY, Glick et al. (eds.), pages 89–119 (CRC Press, 1993), Miki et al., supra, and Moloney et al., *Plant Cell Reports* 8: 238 (1989).

Preferably, expression vectors are introduced into plant tissues using a direct gene transfer method such as microprojectile-mediated delivery, DNA injection, electroporation, and the like. See, for example, Gruber et al., supra; Miki et al., supra; Klein et al., *Biotechnology* 10:268 (1992).

For example, expression vectors can be introduced into plant tissues using microprojectile-mediated delivery with a biolistic device. A generally applicable method of plant transformation is microprojectile-mediated transformation wherein DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, *Trends Biotech.* 6:299 (1988), Sanford, *Physiol. Plant* 79:206 (1990), and Klein et al., *Biotechnology* 10:268 (1992).

Transcription of the foreign gene may be controlled 3.0 by a plant promoter or by a viral promoter, such as a Cauliflower Mosaic Virus (CaMV) 35S promoter and its derivative, the enhanced 35S version ("E35S"), a Figwort Mosaic Virus promoter, and the like. Gruber et al., supra. Odell et al., *Nature* 313:810 (1985); Kay et al., *Science* 236:1299 (1987). The polyubiquitin gene promoters from *Arabidopsis thaliana*, UBQ3 and UBQ10, Norris et al., *Plant Mol. Biol.* 21:895 (1993), are also useful for directing gene expression in transgenic poinsettia. Additional useful promoters from *Arabidopsis* include the TEFA 1 gene promoter from the *Arabidopsis* translation elongation factor 1 gene and two additional polyubiquitin gene promoters from *Arabidopsis*, UBQ11 and UBQ14. Norris et al., *Plant Mol. Biol.* 21:895 (1993); Callis et al., *Genetics* 139:921 (1995). Of these promoters, the preferred promoters are the 35S promoter, the E35S promoter, the UBQ3 promoter, and the UBQ10 promoter.

Other promoters that are useful for phloem-specific expression of transgenes in poinsettia include the rolC gene promoter from *Agrobacterium rhizogenes* and the Commelina Yellow Mottle Virus (CoYMV) promoter which have been shown to direct high levels of transgene expression in the phloem of transgenic plants. Medberry and Olszewski, *Plant J.* 3:619 (1993); Nilsson et al., *Plant Mol. Biol.* 31:887 (1996).

In order to select transformed cells, the expression vector contains a selectable marker gene, such as a herbicide resistance gene or an antibiotic resistance gene. For example, the neomycin phosphotransferase gene (nptII gene) confers resistance to kanamycin and G418, the aminoglycoside phosphotransferase IV gene (hygromycin phosphotransferase gene of *E. coli*) confers resistance to hygromycin, the phosphinothricin acetyltransferase gene confers resistance to phosphinothricine, the dihydrofolate reductase gene confers resistance to methotrexate, the 5-enolpyruvylshikimate-3-phosphate synthase gene confers resistance to glyphosate, the acetohydroxyacid synthase gene confers resistance to sulfonyl ureas and imidazolinones, chloramphenicol resistance is provided by the chloramphenicol acetyltransferase gene, and the 3"-adenylyltransferase gene confers resistance to spectinomycin and streptomycin. Fraley et al., *Proc. Natl. Acad. Sci. U.S.A.* 80:4803 (1983). Gritz and Davies, *Gene* 25:179 (1983), Wilmink and Dons, *Plant Molec. Biol. Report.* 11:165 (1993).

Additional selectable marker genes of bacterial origin that confer resistance to antibiotics include gentamycin acetyltransferase, streptomycin phosphotransferase, aminoglycoside-3'-adenyl transferase, the bleomycin resistance determinant. Hayford et al., *Plant Physiol.* 86:1216 (1988), Jones et al., *Mol. Gen. Genet.* 210:86 (1987), Svab et al., *Plant Mol. Biol.* 14:197 (1990), Hille et al., *Plant Mol. Biol.* 7:171 (1986). Other selectable marker genes confer resistance to herbicides such as glyphosate, glufosinate or broxynil. Comai et al., *Nature* 317:741 (1985), Gordon-Kamm et al., *Plant Cell* 2:603 (1990), and Stalker et al., *Science* 242:419 (1988).

The use of such selectable marker genes is well-known to those of skill in the art. See, for example, Christou, "Application to Plants," in PARTICLE BOMBARDMENT TECHNOLOGY FOR GENE TRANSFER, Yang et al. (eds)., pages 71–99 (Oxford University Press 1994). The hygromycin phosphotransferase ("hph") gene is a preferred selectable marker.

Post-transcriptional events such as processing of the 3'-end of a transcript and polyA addition are important steps of gene expression. Accordingly, expression vectors typically include DNA elements that control the processing of transcripts, such as a transcription termination/polyadenylation sequence. The 3'-flanking region from the nopaline synthase gene (nos) of *Agrobacterium tumefaciens* has proven to be a very efficient and versatile cis-acting sequence for transgene expression.

The expression vector can contain cDNA sequences encoding a foreign protein, as well as the selectable marker gene each under the control of a different promoter. Alternatively, the selectable marker gene can be delivered to host cells in a separate selection expression vector by co-transformation with both vectors.

The present invention also contemplates the production of transgenic poinsettia comprising an expression vector that produces antisense RNA. The binding of antisense RNA molecules to target mRNA molecules results in hybridization arrest of translation. Paterson, et al., *Proc. Natl. Acad. Sci. USA,* 74: 4370 (1987). A suitable antisense RNA molecule, for example, would have a sequence that is complementary to that of a viral mRNA species encoding a protein necessary for proliferation of the virus.

Alternatively, an expression vector can be constructed that produces a ribozyme. Ribozymes can be designed to express endonuclease activity that is directed to a certain target sequence in a mRNA molecule. For example, Steinecke et al., *EMBO J.* 11:1525 (1992), achieved up to 100% inhibition of neomycin phosphotransferase gene expression by ribozymes in tobacco protoplasts. Similarly, Perriman et al., *Antisense Research and Development* 3:253 (1993), inhibited chloramphenicol acetyltransferase activity in tobacco protoplasts using a vector that expressed a modified hammerhead ribozyme. In the context of the present invention, appropriate target RNA molecules for ribozymes include mRNA species that encode viral proteins.

In another approach to providing protection against virus infection, expression vectors can be constructed in which a promoter directs the production of RNA transcripts capable of stimulating RNase P-mediated cleavage of target mRNA molecules. According to this approach, an external guide sequence can be constructed for directing the endogenous ribozyme, RNase P, to a particular species of intracellular mRNA, which is subsequently cleaved by the cellular ribozyme. Altman et al., U.S. Pat. No. 5,168,053. Yuan et al., *Science* 263: 1269 (1994). Preferably, the external guide sequence comprises a ten to fifteen nucleotide sequence complementary to an mRNA species that encodes a protein essential for viral reproduction, and a 3'-NCCA nucleotide sequence, wherein N is preferably a purine. The external guide sequence transcripts bind to the targeted mRNA species by the formation of base pairs between the mRNA and the complementary external guide sequences, thus promoting cleavage of mRNA by RNase P at the nucleotide located at the 5'-side of the base-paired region.

According to the general procedure for producing transgenic poinsettia, epidermal callus cells are cultured and bombarded with at least one type of expression vector that comprises a selectable marker gene. One standard method for obtaining poinsettia callus is described by Preil, "In Vitro Culture of Poinsettia," in THE SCIENTIFIC BASIS OF POINSETTIA PRODUCTION, Strømme (ed.), pages 49–56 (The Agricultural University of Norway 1994).

The somatic embryogenesis methods of Preil can be used to produce both embryos and embryonic callus tissue. A preferred approach, however, is to use the modifications of the Preil method, as described herein, which provides a genotype-independent method of producing large quantities of somatic embryos which can be used to regenerate plants. Such modifications include the addition of casein hydrosylate to the embryo induction medium, which both shortens the Preil protocol and enhances the rate of somatic embryogenesis. In addition, studies indicated that such a modified Preil method is most efficient when applied to Angelika. To obtain quality embryos from cultures of other varieties, such as Jolly Red, Lilo and Freedom, it was necessary to modify auxin and cytokinin in media. For example, media used to induce Angelika somatic embryogenesis contained about 0.5 mg/liter 1-naphthalene acetic acid and about 0.2 mg/liter 6-benzylaminopurine, while somatic embryogenesis of Freedom and Jolly Red tissues was found to be optimal in media containing about 0.8 mg/liter 1-naphthalene acetic acid and about 0.4 mg/liter 6-benzylaminopurine. It was also found that the quality and yield of embryos could be enhanced by modifying embryo development medium. Accordingly, gelling agent concentration and the nitrogen salt ratio were modified, and mannitol was added to increase osmotic pressure of the medium.

The modified procedures described herein produce highly embryogenic callus from induced somatic embryos. In addition to such modifications of the Preil protocol, the methods described herein include an embryo maturation treatment. In brief, embryos that have reached at least the heart-shaped stage are transferred from developmental medium to a medium that contains abscisic acid and high sucrose levels. The embryos are then incubated in this medium for at least six weeks. This additional treatment improves embryo germination uniformity and confers a high degree of desiccation tolerance.

The transformation methods of the instant invention can be used with diverse genotypes of poinsettia. Although it is possible to transform embryogenic callus from shoot tips, stem segments, or immature somatic embryos, higher and more consistent transformation frequencies are obtained when reddish epidermal callus, obtained from mature somatic embryos, is the preferred target for transformation.

According to one transformation method of the present invention, any poinsettia tissue explant capable of producing reddish epidermal callus in vitro, including immature or mature embryos, shoot tips, or stem segments, are incubated in callus induction medium which may be based on a medium described by Murashige and Skoog, *Physiol. Plant* 15: 473 (1962) (MS Medium) supplemented with about 0.5–0.8 mg/liter 1-naphthalene acetic acid, about 0.2–0.4 mg/liter 6-benzylaminopurine and about 1 gm/liter casein hydrosylate. The poinsettia tissue explants are generally incubated on callus induction medium for approximately 4 weeks. The composition of a suitable callus induction medium is shown in Table 1. Reddish epidermal callus, which is embryogenic, is subcultured and incubated on embryo induction medium which may be based on MS medium supplemented with about 0.5–0.8 mg/liter 1-naphthalene acetic acid, about 0.2–0.4 mg/liter 6-benzylaminopurine, about 1 gm/liter casein hydrolysate; 400 to 1700 mg/liter $NH_4NO_3$ and 1900 to 3500 mg/liter KNO3. The composition of a suitable embryo induction medium is shown in Table 2. Somatic embryos begin to form during incubation on embryo induction medium. The reddish epidermal callus is incubated on embryo induction medium for 3 to 4 weeks. The total number of embryos can be increased by repeated culture, one or more times, on callus induction medium for approximately 4 weeks followed by incubation on embryo induction medium for 3 to 4 weeks. Embryogenic callus is preferably transformed soon after subculture from callus induction medium to embryogenic callus induction medium.

Alternatively, or additionally, the total number of somatic embryos can be further increased by subculture of macerated reddish epidermal callus into liquid embryo induction medium. Following approximately 2 to 3 weeks of growth, the cell culture is filtered through 2000, 1000 and 500 μm filters and the filtrate is subcultured into fresh liquid embryo induction medium and cultured for approximately 1 to 3 weeks. The cell culture is once again filtered through 2000, 1000 and 500 μm filters and the filtrate is subcultured on to solid developmental induction medium and cultured for approximately 2 weeks. The somatic embryos at this point in the protocol are generally in the heart-shaped to torpedo stage. The somatic embryos are transferred to maturation medium and cultured for approximately 6 weeks until the embyos are mature. The composition of a suitable maturation medium is shown in Table 4. In preparation for transformation, the mature embryos are transferred to callus induction medium for approximately 3 weeks and then reddish epidermal callus subcultured on to embryo induction medium. The cells are transformed, preferably by microparticle bombardment, soon after subculture to embryo induction medium.

Following transformation, for example, by microparticle bombardment, the presumptively transformed cells are transferred to selection medium comprising about 0.5–0.8 mg/liter 1-naphthalene acetic acid, about 0.2–0.4 mg/liter 6-benzylaminopurine, about 1 gm/liter casein hydrosylate and a selection agent. The presumptively transformed cells are cultured for approximately 2 weeks on selection medium. The developing embryos are then transferred to developmental medium which may be a MS-based medium comprising about 0.05 gm/liter 6-benzylaminopurine and about 10 gm/liter mannitol. The composition of a suitable developmental medium is shown in Table 3. The developmental medium may contain a selection agent. The embryos are then transferred to maturation medium which may contain a selection agent. Finally, transgenic plantlets are produced from the matured somatic embryos.

As an illustration, the following procedure can be used to produce transgenic poinsettia cv. Angelika. Shoot tip or stem segments from Angelika are incubated in callus induction medium which may be based on a MS medium supplemented with about 0.5 mg/liter l-naphthalene acetic acid, about 0.2 mg/liter 6-benzylaminopurine and about 1 gm/liter casein hydrosylate. A suitable callus induction medium is shown in Table 1. The shoot tip or stem segments are generally incubated on callus induction medium for approximately 4 weeks.

In order to obtain more highly embryogenic epidermal callus, the embryogenic callus may be cultured on callus induction medium for approximately 4 weeks followed by culture on callus induction medium for approximately 4 weeks. Subculture on callus induction medium followed by embryo induction medium may be repeated one or more times in order to obtain more highly embryogenic callus.

TABLE 1

Callus Induction Medium[a][b]

| Component | Concentration (mg/liter) |
|---|---|
| $NH_4NO_3$ | 1650 |
| $KNO_3$ | 1900 |
| $MgSO_4.7H_2O$ | 370 |
| $MnSO_4.H_2O$ | 17.0 |
| $ZnSO_4.7H_2O$ | 10.6 |
| $CuSO_4.5H_2O$ | 0.025 |
| $CaCl_2.2H_2O$ | 440 |
| $CoCl_2.6H_2O$ | 0.025 |
| KI | 0.83 |
| $KH_2PO_4$ | 170 |
| $H_3BO_3$ | 6.2 |
| $Na_2MoO_4.2H_2O$ | 0.25 |
| $FeSO_4.7H_2O$ | 27.8 |
| disodium EDTA | 37.2 |
| nicotinic acid | 0.5 |
| thiamine | 0.1 |
| pyridoxine | 0.5 |
| 1-naphthalene acetic acid | 0.5 |
| 6-benzylaminopurine | 0.2 |
| sucrose | 30,000 |
| myo-inositol | 100 |
| casein hydrosylate | 1,000 |

[a]pH 5.8
[b]For dark leaf varieties of poinsettia, such as Freedom, Regal Velvet or 671G, the medium should contain 0.8 mg/l 1-naphthalene acetic acid and either 0.3 or 0.4 mg/l 6-benzylaminopurine.

Reddish epidermal callus which is embryogenic is subcultured and incubated on embryo induction medium which may be based on MS medium supplemented with about 0.5 mg/liter 1-naphthalene acetic acid, about 0.2 mg/liter 6-benzylaminopurine, about 1 gm/liter casein hydrolysate, 400 to 1700 mg/liter $NH_4NO_3$ and 1900 to 3500 mg/liter KNO3. The composition of a suitable embryo induction medium is shown in Table 2. Somatic embryos begin to form during incubation on embryo induction medium. The embryogenic callus is incubated on embryo induction medium for approximately 4 weeks.

TABLE 2

Embryo Induction Medium[a,b]

| Component | Concentration (mg/liter) |
| --- | --- |
| $NH_4NO_3$ | 412 |
| $KNO_3$ | 3,464 |
| $MgSO_4.7H_2O$ | 370 |
| $MnSO_4.H_2O$ | 17.0 |
| $ZnSO_4.7H_2O$ | 10.6 |
| $CuSO_4.5H_2O$ | 0.025 |
| $CaCl_2.2H_2O$ | 440 |
| $CoCl_2.6H_2O$ | 0.025 |
| KI | 0.83 |
| $KH_2PO_4$ | 170 |
| $H_3BO_3$ | 6.2 |
| $Na_2MoO_4.2H_2O$ | 0.25 |
| $FeSO_4.7H_2O$ | 27.8 |
| disodium EDTA | 37.2 |
| nicotinic acid | 5.0 |
| thiamine | 5.0 |
| pyridoxine | 0.5 |
| 1-naphthalene acetic acid | 0.5 |
| 6-benzylaminopurine | 0.2 |
| sucrose | 30,000 |
| mannitol | 10,000 |
| myo-inositol | 100 |
| casein hydrosylate | 1,000 |
| agar | 8,000 |

[a]pH 5.87
[b]For dark leaf varieties of poinsettia, such as Freedom, Regal Velvet or 671G, the medium should contain 0.8 mg/l 1-naphthalene acetic acid and either 0.2–0.4 mg/l 6-benzylaminopurine.

Embryogenic callus is transferred to liquid embryo induction medium and incubated with shaking for 2 to 3 weeks. The cells are passed through 2,000, 1,000 and 500 µm filters and the filtrate is transferred to fresh liquid embryogenic callus medium. The cells are incubated for 1 to 3 weeks and then filtered through 2,000, 1,000 and 500 µm filters. The filtrate is incubated on solid embryo induction medium for approximately 2 weeks. The developing embryos are then transferred to maturation medium and cultured for approximately 6 weeks. The composition of a representative maturation medium is shown in Table 4. Mature embryos are produced. These mature embryos are then transferred to callus induction medium and incubated for approximately 3 weeks. Reddish epidermal callus is transferred to an embryo induction medium and transformed.

Cells are preferably transformed by microparticle bombardment. General methods for microparticle bombardment of plant tissue are well-known. See, for example, Miki et al., "Procedures for Introducing Foreign DNA into Plants," in METHODS IN PLANT MOLECULAR BIOLOGY AND BIOTECHNOLOGY, Glick et al. (eds.), pages 67–88 (CRC Press 1993), and Christou, "Application to Plants," in PARTICLE BOMBARDMENT TECHNOLOGY FOR GENE TRANSFER, Yang et al. (eds.), pages 71–99 (Oxford University Press 1994). Cells are transferred from callus induction to embryo induction media, and soon thereafter, preferably within one week, the cells are bombarded with microprojectiles coated with at least one type of expression vector.

The examples described herein provide a particular method for bombardment of poinsettia tissue. General parameters that are significant for bombardment of poinsettia tissue include bombardment of callus once at a pressure of 1200 psi and a particle flight distance of 9 cm. Each plate was bombarded with 100 ng DNA (50 ng gene of interest and 50 ng selectable marker).

One week after bombardment, cells are transferred to developmental medium containing a selection agent. For example, the medium contains about 10 mg/liter hygromycin if the selectable marker is aminoglycoside phosphotransferase IV. The compositions of a suitable developmental medium is shown in Table 3. After an incubation of about two weeks, plant material is macerated and transferred to liquid developmental medium for approximately 18 to 24 hours.

TABLE 3

Developmental Medium[a]

| Component | Concentration (mg/liter) |
| --- | --- |
| $NH_4NO_3$ | 138 |
| $KNO_3$ | 4,000 |
| $MgSO_4.7H_2O$ | 370 |
| $MnSO_4.H_2O$ | 17.0 |
| $ZnSO_4.7H_2O$ | 10.6 |
| $CuSO_4.5H_2O$ | 0.025 |
| $CaCl_2.2H_2O$ | 440 |
| $CoCl_2.6H_2O$ | 0.025 |
| KI | 0.83 |
| $KH_2PO_4$ | 170 |
| $H_3BO_3$ | 6.2 |
| $Na_2MoO_4.2H_2O$ | 0.25 |
| $FeSO_4.7H_2O$ | 27.8 |
| disodium EDTA | 37.2 |
| nicotinic acid | 5.0 |
| thiamine | 5.0 |
| pyridoxine | 0.5 |
| 6-benzylaminopurine | 0.05 |
| sucrose | 30,000 |
| mannitol | 10,000 |
| myo-inositol | 100 |
| casein hydrosylate | 1,000 |

[a]pH 5.8

After 18–24 hours incubation with shaking, somatic embryos are recovered and cultured on developmental medium for approximately 2 weeks followed by incubation on maturation medium. The composition of a suitable maturation medium is shown in Table 4. The embryos are allowed to mature for about six weeks to allow germination into plantlets

TABLE 4

Maturation Medium[a]

| Component | Concentration (mg/liter) |
| --- | --- |
| $NH_4NO_3$ | 138 |
| $KNO_3$ | 4,000 |
| $MgSO_4.7H_2O$ | 370 |
| $MnSO_4.H_2O$ | 17.0 |
| $ZnSO_4.7H_2O$ | 10.6 |
| $CuSO_4.5H_2O$ | 0.025 |
| $CaCl_2.2H_2O$ | 440 |
| $CoCl_2.6H_2O$ | 0.025 |
| KI | 0.83 |
| $KH_2PO_4$ | 170 |
| $H_3BO_3$ | 6.2 |
| $Na_2MoO_4.2H_2O$ | 0.25 |
| $FeSO_4.7H_2O$ | 27.8 |
| disodium EDTA | 37.2 |
| nicotinic acid | 5.0 |
| thiamine | 5.0 |
| pyridoxine | 0.5 |
| abscisic acid | 5–20 |
| sucrose | 60,000 |
| mannitol | 10,000 |

TABLE 4-continued

Maturation Medium[a]

| Component | Concentration (mg/liter) |
|---|---|
| myo-inositol | 100 |
| casein hydrosylate | 1,000 |
| Gelrite | 2,000 |

[a]pH 5.8

The above procedure can be optimized for cultivars other than Angelika. For example, the production of transgenic Freedom would contain the following modifications of the protocol: (1) callus is generated from shoot tip and stem segments by incubation in Ms medium that contains 0.8 mg/liter 1-naphthalene acetic acid, 0.4 mg/liter 6-benzylaminopurine, and 6 mg/liter agar, (2) callus cells are incubated in medium that contains 0.8 mg/liter 1-naphthalene acetic acid, 0.4 mg/liter 6-benzylaminopurine, 825 mg/liter $NH_4NO_3$, 2942 mg/liter $KNO_3$, 10 mg/liter mannitol and 8 gm/liter agar, (3) suspension culture medium contains 0.8 mg/liter 1-naphthalene acetic acid, 0.4 mg/liter 6-benzylaminopurine, 825 mg/liter $NH_4NO_3$, 2942 mg/liter $KNO_3$ and 10 gm/liter mannitol, (4) somatic embryos are cultured on MS medium comprising 0.8 mg/liter 1-naphthanblene acetic acid, 0.4 mg/liter 6-benzylaminopurine and 6 gm/liter agar, (5) prior to bombardment, callus is incubated for three weeks in embryo induction medium that contains 0.8 mg/liter 1-naphthalene acetic acid, 0.2 mg/liter 6-benzylaminopurine, 825 mg/liter $NH_4NO_3$, 2942 mg/liter $KNO_3$ and 3.5 gm/liter Gelrite, and (5) one week after bombardment, embryos are transferred to medium containing 0.8 mg/liter 1-naphthalene acetic acid, 0.2 mg/liter 6-benzylaminopurine, 825 mg/liter $NH_4NO_3$, 2942 mg/liter $KNO_3$ and a selection agent (e.g., 10 mg/liter hygromycin).

An alternative method for regenerating poinsettia involves directly transferring reddish epidermal callus containing embryos from embryo induction medium to developmental medium. In this method, the incubation step in liquid medium is eliminated. Likewise, transgenic poinsettia plants can be produced in a method that eliminates the incubation step in liquid medium. Following introduction of an expression vector into reddish epidermal callus containing embryos, the transformed callus is transferred to selection medium. The transformed callus is then transferred to developmental medium. Finally, the transformed callus is transferred to maturation medium and plantlets are recovered from the embryos.

Such methods can be used to produce transgenic poinsettia from any well-known, commercially available cultivars including Peace Jolly Red, Peace Cheers, and Red Splendor (Ball Flora Plant). Other suitable poinsettia cultivars include Gutbier Angelika Red, Eckespoint Freedom Red, Eckespoint Red Sails, Eckespoint Pink Peppermint, Eckespoint Jingle Bells 3, Gross Supjibi, Gutbier V14 Glory, Gutbier V17 Marble, Eckespoint Lilo Pink, and Gutbier V17 Angelika White (Ecke).

Transgenic poinsettia are propagated using standard methods. As an illustration, plants can be propagated by rooting tip cuttings from branches of vegetative stock plants. See, for example, Dole, "Stock Plant Management and Cutting Production—Scientific and Applied Concepts," in THE SCIENTIFIC BASIS OF POINSETTIA PRODUCTION, Strømme (ed.), pages 31–37 (The Agricultural University of Norway 1994); Gislerød, "The Rootings of Poinsettia Cuttings and the Physical Conditions of the Substrate," in THE SCIENTIFIC BASIS OF POINSETTIA PRODUCTION, Strømme (ed.), pages 39–43 (The Agricultural University of Norway 1994); and Ecke, Jr. et al. (eds.), THE POINSETTIA MANUAL, 3rd Edition (Paul Ecke Productions 1990).

4. Production of Transgenic Poinsettia Expressing a Foreign Gene that Enhances Commercial Value (a) Inhibition of Plant Pests and Diseases The present invention provides a means to control insect pests and diseases of poinsettia plants. Poinsettias are subject to attack by insect pests and pathogen-induced diseases under greenhouse conditions. One of the most serious insect pests is the whitefly, including the greenhouse whitefly (*Trialeurodes vaporariorum*), the sweetpotato whitefly (*Bemesia tabaci*), and the banded wing whitefly (*Trialeurodes abutilonia*). The adult whitefly damages poinsettia plants by withdrawing sap from leaf phloem. Mealybugs, such as the citrus mealybug (*Planococcus citri*), the Mexican mealybug (*Phenacoccus gossypii*), the grape mealybug (*Pseudococcus maritimus*) and the longtail mealybug (*Pseudococcus longispinus*) also damage poinsettia plants by withdrawing sap.

Thrip adults and larvae feed by withdrawing plant cell contents. The affected plant cells fill with air, distorting the leaves. Similarly, aphids, such as the green peach aphid (*Myzus persicae*) and the root aphid (*Pemphigus* species) and scales take in plant fluids causing distortion or curling of the leaves. Aphids are also known to be plant virus carriers. Spider mites, including the two-spotted spider mite (*Tetranychus urticae*) and the Lewis mite (*Eotetranychus lewisi*) puncture leaf cells, causing the leaves to dry and become parchment-like.

Fungus gnats (*Bradysia* species) produce larvae that feed on tender roots, stem and leaf tissue, causing cuttings and plants to whither and die. Many types of lepidopterous larvae (worms) also attack greenhouse poinsettia plants. For example, the cutworm attacks all parts of the plant. The omnivorous looper (*Tortrix*) is another worm that feeds on poinsettia.

Insect infestation also produces secondary effects which place the plant at risk. For example, whiteflies, mealybugs and aphids excrete honeydew, which is an excellent growing medium for the development of sooty mold. Honeydew also attracts ants, which in turn, can spread pests such as aphids, mealybugs and scales from plant to plant.

Poinsettia are also susceptible to diseases caused by fungi and bacteria. *Rhizoctonia* root and stem rot (*Rhizoctonia solani*) and *Pythium* root and stem rot (*Pythium* species) can induce defoliation and complete collapse of the poinsettia. All parts of a poinsettia plant are susceptible to attack by fungi such as *Phytophthora* crown and stem rot (*Phytophthora parasitica*), *Botrytis* blight ("gray mold"; *Botrytis cineria*), *Rhizopus* blight (*Rhizopus stolonifera*), *Choanephora* wet rot (*Choanephora cucurbitarium*), and black root rot (*Thielaviopsis basicola*). Powdery mildew, a fungal disease, is also a significant poinsettia pathogen.

Although certain fungal infections may not cause the complete destruction of a poinsettia plant, the diseases can destroy the ornamental, and therefore commercial, value of the plant. As an illustration, poinsettia scab (*Sphaceloma poinsettiae*) induces lesions on stems, Corynespora bract spot (*Corynespora cassiicola*) causes the appearance of brown lesions on leaves, while *Alternaria* blight of poinsettia (*Alternaria euphorbiicola*) induces lesions in all aboveground plant parts. Powdery mildew causes a powdery appearance of leaves and bracts.

Bacteria infect poinsettia primarily through wounds such as the surface of a cutting made for vegetative propagation, or natural openings, such as hydathodes, lenticels, nectaries, and stomates. Significant poinsettia bacterial pathogens include *Erwinia carotovora* (bacterial soft rot), *Corynebacterium flaccumfaciens* pv. *poinsettiae* (bacterial canker), *Xanthomonas campestris* pv. *poinsettiaecola* (bacterial leaf spot), *Pseudomonas viridiflava* (greasy canker), and *Erwinia chrysanthemi* (bacterial stem rot).

Two notable viral pests of poinsettia are the Poinsettia Mosaic Virus and the Poinsettia Cryptic Virus. Although infections typically do not produce destructive symptoms, the presence of a poinsettia virus can affect the morphology of the plant. Depending upon the commercial use, therefore, it may be desirable to inhibit the growth of poinsettia viruses.

As a protection against insect pests, transgenic poinsettia can be produced that express insecticidal toxin genes. For example, the gram-positive bacterium *Bacillus thuringiensis* produces polypeptides that are toxic to a variety of insect pests, but have no activity against vertebrates and beneficial insects. Thompson, "Biological Control of Plant Pests and Pathogens: Alternative Approaches," in BIOTECHNOLOGY IN PLANT DISEASE CONTROL, Chet (ed.), pages 275–290 (Wiley-Liss, Inc. 1993). Suitable *Bacillus thuringiensis* toxins include cryIA δ-endotoxins which are highly toxic to lepidopteran insects and cryIIIA δ-endotoxins which are highly toxic to coleopteran insects.

Geiser et al., *Gene* 48: 109 (1986), disclose the cloning and nucleotide sequence of a cryIA(b) δ-endotoxin gene. The transformation of plants with vectors comprising a cryIA(b) δ-endotoxin gene has been described by Williams et al., *Bio/Technology* 10: 540 (1992), Koziel et al., *Bio/Technology* 11: 194 (1993), and Fujimoto et al., *Bio/Technology* 11: 1151 (1993). Lereclus et al., *Bio/Technology* 10: 418 (1992), disclose the construction of a plasmid comprising structural genes encoding for cryIIIA and cryIAc. In addition, Adang et al., *Plant Molec. Biol.* 21: 1131 (1993), disclose the nucleotide sequence of a synthetic cryIIIA gene which was designed for optimal expression in plant cells. Moreover, DNA molecules encoding δ-endotoxin genes can be purchased from American Type Culture Collection (Rockville, Md.), under ATCC accession Nos. 40098, 67136, 31995 and 31998.

The following list provides other insecticidal toxins which are suitable for production of transgenic poinsettia.

(1) A vitamin-binding protein such as avidin.

(2) An enzyme inhibitor, for example, a protease inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), and Sumitani et al., *Biosci. Biotech. Biochem.* 57:1243 (1993) (nucleotide sequence of *Streptomyces nitrosporeus* α-amylase inhibitor).

(3) An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

(4) An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also Tomalski et al., U.S. Pat. No. 5,266,317, who disclose genes encoding insect-specific, paralytic neurotoxins.

(5) An insect-specific venom produced in nature by a snake, a wasp, etc. For example, see Pang et al., *Gene* 116:165 (1992), for disclosure of heterologous expression in plants of a gene to coding for a scorpion insectotoxic peptide.

(6) An enzyme responsible for an hyperaccumulation of a monoterpene, a sesquiterpene, a steroid, hydroxamic acid, a phenylpropanoid derivative or another non-protein molecule with insecticidal activity.

(7) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See Scott et al., PCT application WO 93/02197, who disclose the nucleotide sequence of a callase gene. DNA molecules which contain chitinase-encoding sequences can be obtained, for example, from the ATCC under accession Nos. 39637 and 67152. See also Kramer et al., *Insect Biochem. Molec. Biol.* 23:691 (1993), who teach the nucleotide sequence of a cDNA encoding tobacco hookworm chitinase, and Kawalleck et al., *Plant Molec. Biol.* 21:673 (1993), who provide the nucleotide sequence of the parsley ubi4-2 polyubiquitin gene.

(8) A molecule that stimulates signal transduction.

For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

(9) An insect-specific antibody or an immunotoxin derived therefrom. Thus, an antibody targeted to a critical metabolic function in the insect gut would inactivate an affected enzyme, killing the insect. Cf. Taylor et al., Abstract #497, SEVENTH INT'L SYMPOSIUM ON MOLECULAR PLANT-MICROBE INTERACTIONS (1994) (enzymatic inactivation in transgenic tobacco via production of single-chain antibody fragments).

As discussed above, chitinase genes are useful for inhibiting insect pests. Chitinase also can be used for combating fungal pathogens. Methods for producing transgenic plants that express chitinase are described, for example, by Suslow et al., U.S. Pat. No. 5,554,521 (1996), and by Jaynes et al., U.S. Pat. No. 5,597,946 (1997). Additional antifungal genes include genes encoding β-1,3-glucanase, which degrades a major polysaccharide of fungal cell walls, and ribosome-inactivating protein, which inactivates fungal ribosomes. Full-length cDNAs of glucanase and ribosome-inactivating protein are disclosed in Leah et al., *J. Biol. Chem.* 266:1564 (1991). In addition, Logemann et al., *Bio/Technology* 10:305 (1992), demonstrate that the expression of a foreign ribosome-inactivating protein increases resistance to fungal disease in transgenic plants.

Those of skill in the art are aware of additional polypeptides useful to protect plants against bacterial and fungal pathogens. See, for example, Düring, *Molec. Breeding* 2:297 (1996). Such polypeptides include the bactericidal native and recombinant cecropins, insect attacin, frog magainin, cereal thionins, T4 and hen egg white lysozymes, horseshoe crab tachyplesin I, *Erwinia* oligogalacturonide lyase. Moreover, a variety of plant disease resistance genes are available for use. Bent, *The Plant Cell* 8:1757 (1996).

Preferred antibacterial and antifungal genes include DNA molecules that encode natural and synthetic lytic peptides and plant defensins. Lytic peptides are broad-spectrum antibiotic peptides that are active against Gram-negative and Gram-positive bacteria, fungi and protozoa. These peptides can be classified into many categories based upon their structure (e.g., linear vs. cyclic), their size (20–45 amino acids) and their source (e.g., insect, amphibian, plant). However, despite their apparent diversity, numerous defense-related peptides have the common features of being highly basic and being capable of forming amphipathic structures. These unifying features suggest that most peptides appear to act by a direct lysis of the pathogenic cell membrane. Their basic structure facilitates their interaction with the cell membrane, and their amphipathic nature allow them to be incorporated into the membrane ultimately disrupting its structure.

Frog skin secretions of the African clawed frog, *Xenopus laevis*, have been discovered to be a particularly rich source of antibiotic peptides. Known peptides include magainins, PGL$^a$, xenopsin, and caerulein. Gibson et al., *J. Biol. Chem.* 261:5341 (1986); Jacob and Zasloff, *Ciba Found. Symp.* 186:197 (1994); James et al., *Anal. Biochem.* 217:84 (1994); Maloy and Kari, *Biopolymers* 37:105 (1995); Wechselberger and Kreil, *J. Molec. Endocrinol.* 14:357 (1995). Magainins 1 and 2 have 23 amino acid residues in length, contain no cysteine, and form an amphipathic α-helix. PGL$^a$ is a small peptide processed from a larger precursor and is both cationic and amphipathic in nature. It has the somewhat unusual feature of containing a COOH-terminal amide group rather than the expected carboxyl group. Moreover, it has been reported that magainin 2 (but not magainin 1) and PGL$^a$ can interact synergistically with one another to exert enhanced levels of anti-microbial activity. Westerhoff et al., *Eur. J. Biochem.* 228:257 (1995).

Insects have also been demonstrated to possess a variety of defense-related peptides. Cecropins from moths and flies are slightly larger than the frog-derived peptides (31–39 residues), are basic due to the presence 1:5 of multiple arginine and lysine residues, and therefore interact strongly with the negatively charged lipid bilayers. Boman, *Cell* 65:205 (1991). Studies of these peptides have shown that they form an N-terminal α-helical region connected by a hinge region to a C-terminal α-helical domain.

In addition to the naturally-occurring peptides, a wide array of synthetic analogs representing deletion, substitution and variable chain length derivatives have been generated for structure/activity relationship studies. A number of these synthetic variants exhibit increased antimicrobial activity against bacteria and fungi. Moreover, in some cases, not only has the anti-microbial potency of the synthetic lytic peptides increased dramatically, but their spectrum of anti-microbial activity has also broadened.

As described herein, a series of magainin-, PGL$^a$-, and cecropin-type lytic peptides were evaluated for anti-microbial activity against a wide range of bacterial and fungal phytopathogens. These peptides, chemically synthesized and purified to homogeneity, included both natural peptides and substitution derivatives. The primary amino acid sequence of magainin 2, a naturally-occurring peptide, is: GLY-ILE-GLY-LYS-PHE-LEU-HIS-SER-ALA-LYS-LYS-PHE-GLY-LYS-ALA-PHE-VAL-GLY-GLU-ILE-MET-ASN-SER (SEQ ID NO:1). The peptide, PGL is a synthetic version of PGL$^a$, which contains a COOH group at its C-terminus to approximate the peptide synthesized in plants. The amino acid sequence of PGL is: GLY-MET-ALA-SER-LYS-ALA-GLY-ALA-ILE-ALA-GLY-LYS-ILE-ALA-LYS-VAL-ALA-LEU-LYS-ALA-LEU (SEQ ID NO:2).

MSI-99 and MSI-55 are synthetic analogs of magainin 2 and PGL, respectively. Amino acid differences between magainin 2 and MSI-99 are highlighted in bold in the following MSI-99 amino acid sequence: GLY-ILE-GLY-LYS-PHE-LEU-LYS-SER-ALA-LYS-LYS-PHE-GLY-LYS-ALA-PHE-VAL-LYS-[ ]-ILE-LEU-ASN-SER (SEQ ID NO:3). MSI-55 has the following amino acid sequence: LYS-ILE-ALA-GLY-LYS-ILE-ALA-LYS-ILE-ALA-GLY-LYS-ILE-ALA-LYS-ILE-ALA-GLY-LYS-ILE-ALA (SEQ ID NO:4). D5-C, a synthetic analog of cecropin B, has the following amino acid sequence: LYS-ARG-LYS-ARG-ALA-VAL-LYS-ARG-VAL-GLY-ARG-ARG-LEU-LYS-LYS-LEU-ALA-ARG-LYS-ILE-ALA-ARG-LEU-GLY-VAL-ALA-PHE (SEQ ID NO:5).

As described below, magainin 2, PGL, MSI-99, MSI-55 and D5-C were tested against a variety of phytopathogenic microbes. In addition, the combination of magainin 2 and PGL was tested to assess whether enhanced anti-microbial activity was observed with this mixture.

The isolation and characterization of plant defensins from a number of plant species has revealed that these small peptides possess potent anti-microbial activity. Broekaert et al., *Plant Physiol.* 108:1353 (1995); Epple et al., *FEBS Lett.* 400:168 (1997). One of these defensins, Rs-AFP2 from radish seeds, has been extensively characterized. Terras et al., *Plant Cell* 7:573 (1995). A cDNA molecule that encodes this peptide has been cloned and overexpressed in tobacco. Transgenic tobacco which accumulate high levels of this peptide show enhanced resistance to infection by the fungal pathogen, *Alternaria longipes*.

Preferred insect resistance genes include DNA molecules that encode tryptophan decarboxylase (TDC) and lectins. TDC catalyzes the decarboxylation and conversion of L-tryptophan into tryptamine. Tryptamine and secologanin, another secondary compound, are then condensed to form strictosidine, the precursor for all terpenoid indole alkaloids in *Catharanthus roseus* (periwinkle). The cloning and characterization of a TDC cDNA molecule from *Catharanthus* seedlings has been described by De Luca et al., *Proc. Nat'l Acad. Sci. USA* 86:2582 (1989).

Thomas et al., *Plant Physiol.* 109: 717 (1995) demonstrated that tobacco plants which accumulated tryptamine adversely affected the development and reproduction of *Bemisia tabaci* (sweet potato whitefly). Whitefly emergence tests revealed that pupae emergence (to adulthood) on tryptamine-accumulating plants was typically reduced three to seven-fold relative to control plants. They speculated that tryptamine may exert its anti-whitefly effect(s) during either larval and pupal development and/or adult selection of a leaf for feeding and oviposition. Studies with the TDC gene are presented below.

An alternative anti-whitefly strategy focuses on the use of lectins to disrupt the normal life cycle of insect pests. A considerably large number of artificial feeding studies have shown that a wide range of insects are susceptible to these compounds. One particular lectin, isolated from *Galanthus nivalis* (snowdrop plant), has been demonstrated to exhibit anti-insect activity against phloem-feeders like aphids and leafhoppers. The production of transgenic poinsettia that express GNA lectin is described below.

In one approach for providing protection against viral infections, transgenic poinsettia express a viral protein. The accumulation of viral coat or replicase proteins in transformed plant cells provides resistance to viral infection and/or disease development by the virus from which the coat protein gene was derived, as well as by related viruses. See Beachy et al., *Ann. Rev. Phytopathol.* 28: 451 (1990); Beachy, "Virus Resistance Through Expression of Coat Protein Genes," in BIOTECHNOLOGY IN PLANT DISEASE CONTROL, 3rd Edition, Chet (Ed.), pages 89–104 (Wiley-Liss, Inc. 1993). For example, coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus. Id.

Alternatively, protection against viral disease can be achieved using a vector that expresses mammalian 2'–5' oligoadenylate synthetase. Truve et al., *Bio/Technology* 11: 1048 (1993), disclose the cloning and nucleotide sequence of a rat cDNA encoding 2'–5' oligoadenylate synthetase, a component of the mammalian interferon-induced antivirus response. Truve et al., also disclose that transgenic plants expressing 2'–5' oligoadenylate synthetase are protected against viral infection under field conditions.

In a third approach to providing protection against viral infection, a transgenic poinsettia expresses a viral genome antisense RNA. For example, antisense RNA has been used to confer resistance to cucumber mosaic virus, as disclosed by Rezaian et al., *Plant Molec. Biol.* 11: 463 (1988). Moreover, Day et al., *Proc. Nat'l. Acad. Sci.* 88: 6721 (1991), have demonstrated the use of antisense RNA to confer resistance to tomato golden mosaic virus.

In a fourth approach to providing protection against viral infection, a transgenic poinsettia expresses pokeweed antiviral protein (PAP), a ribosome-inhibiting protein found in the cell walls of *Phytolacca americana*. Lodge et al., *Proc. Nat'l Acad. Sci USA* 90: 7089 (1993), for example, show that PAP-expressing transgenic plants are resistant to a broad spectrum of plant viruses. Lodge et al. also disclose a method for isolating PAP cDNA.

(b) Expression of Foreign Genes that Affect Poinsettia Plant Habit, Fragrance and Color.

Poinsettia growers seek to produce plants which are more compact (with short internodes and free branching), earlier to flower, and with bright and distinctly colored bracts. Although poinsettias have not been produced having fragrance, this would be a desirable new consumer trait.

A variety of genes have been shown to create a more compact habit and earlier flowering in transgenic plants. These include the rol genes (A, B, and C) from *Agrobacterium rhizogenes* (U.S. Pat. No. 5,648,598), phytochrome genes such as phyA (McCormac et al., *Planta* 185: 162–170 (1991)), developmental genes such as lfy (Wegel and Nilsson, *Nature* 377: 495–496 (1995)), and the MADS-box containing family of genes such as apetala (Mandel and Yanofski, *Nature* 377: 522–524 (1995)), and OsMADS1 (Chung et. al., *Plant Mol. Biol.* 26: 657–665, (1994)). With the present invention, these genes can be employed to improve the habit and reduce the flowering time of poinsettia, most preferably the genes OsMADS1 or phyA.

A variety of genes have been shown to create modified color expression in transgenic plants. These include the crtO gene which can lead to the synthesis of the bright red pigment called astaxanthin, the lycopene cyclase gene which can lead to the synthesis of the orange pigment β-carotene, the β-carotene hydroxylase gene which can lead to the synthesis of the golden pigment zeaxanthin, as well as the genes in the flavonoid biosynthesis pathway which leads to the various anthocyananin pigments which can be red, blue, pale yellow, as well as a wide range of intermediates and pastels. With the present invention these genes can be employed to expand the color range in poinsettia. The preferred genes are crtO and lycopene cyclase.

Several genes have been cloned which affect plant fragrance. These genes include, but are not limited to, the linalool synthase gene which causes the synthesis of aromatic linalool and the limonene synthase gene which causes synthesis of the fragrant limonene (Alonsa et al., *J. Biol. Chem.* 267: 7582–7587 (1992). With the present invention, genes which affect plant fragrance can be employed to create novel fragrances in poinsettia.

Ethylene is a key regulator in plant growth and development. Ethylene affects seed germination, stem and root elongation, flower initiation, and senescence of leaves and flowers. Many important floricultural products are very sensitive to ethylene, and under current practice, plants are treated with silver thiosulfate to eliminate ethylene sensitivity. This practice, however, is being phased out because the use of silver thiosulfate has negative environmental consequences.

Another means to confer ethylene insensitivity is to produce plants expressing a gene that affects the synthesis or perception of ethylene. Researchers have identified proteins associated with mutations in ethylene receptors or factors involved in ethylene signal transduction. For example, the *Arabidopsis* etr-1 and the tomato NR genes encode mutated receptors that confer dominant ethylene insensitivity. See, for example, Chang et al., *Science* 262: 539 (1993) and Wilkinson et al., *Science* 270: 1807 (1995). Moreover, the report of Wilkinson et al., *Nature Biotechnology* 15: 444 (1997), shows that the etr1-1 causes significant delays in flower senescence and flower abscission when expressed in transgenic petunia plants.

Accordingly, the present invention contemplates the production of transgenic poinsettia expressing a gene that confers ethylene insensitivity. Suitable genes are exemplified by genes that encode mutated ethylene receptors, such as the *Arabidopsis* etr1-1 and the tomato NR genes. Such plants are less likely to suffer injury during shipment or in retail outlet environments and will therefore be of higher quality and more attractive.

Another gene that can be used to enhance poinsettia plants is the *Vitreoscilla* hemoglobin gene ("vhb gene"), which is expressed by bacteria under oxygen-limited conditions. Khosla and Bailey, *Nature* 331:633 (1988). Holmberg et al., *Nature Biotechnology* 15:244 (1997), have shown that transgenic tobacco plants that express the vhb gene exhibit enhanced growth and a reduction in germination time, presumably due to an increased availability of oxygen and/or energy in the plant cells. Accordingly, the present invention also contemplates the production of transgenic poinsettia plants that express the vhb gene.

Cytokinins are believed to play a role in leaf senescence because a decline in leaf cytokine levels occurs in senescing leaves, while the external application of cytokinin can delay senescence. Additional evidence for the role of cytokinins was provided by the demonstration that the expression of a gene encoding isopentenyl transferase, the enzyme that catalyzes the rate-limiting step in cytokinin biosynthesis, in transgenic tobacco inhibited leaf senescence. Gan and Amasino, *Science* 270:1966 (1995). In this study, the expression of the isopentenyl transferase (IPT) gene was specifically targeted to senescing leaves and was negatively autoregulated to prevent overproduction of cytokinins. This was achieved by constructing an expression cassette comprising the IPT gene operatively linked to a promoter of an *Arabidopsis* senescence-associated gene, designated SAG12.

Thus, transgenic poinsettia can be produced that are characterized by a decreased rate of leaf senescence. Such poinsettia plants express the IPT gene, which is under the control of a promoter of a senescence-associated gene, such as the promoter of the SAG12 gene.

Studies have shown that floral organ development is controlled by a group of regulatory factors that contain a conserved MADS box domain, which is believed to be a DNA-binding domain. Schwarz-Sommer et al., *EMBO J.* 11:251 (1992). Genes that contain the MADS domain include the *Antirrhinum majus* PLENA gene, the *A. majus* SQUAMOSA gene, the *A. majus* DEFICIENS A gene, the *A. majus* GLOBOSA gene, the *Arabidopsis thaliana* APTELA1 and APETALA3 genes, the *Arabidopsis* AGAMOUS gene, and rice OsMADS24 and OsMADS45 genes. Bradley et al., *Cell* 72:85 (1993); Huijser et al., *EMBO J.* 11:1239 (1992); Brochman et al., *Cell* 68:683 (1992); Mandel et al., *Nature* 360:273 (1992); Sommer et al., *EMBO J.* 9:605 (1990); Trobner et al., *EMBO J.* 11:4693 (1992); Yanofsky et al., *Nature* 346:35 (1990); Greco et al., *Mol. Gen. Genet.* 253:615 (1997).

Chung et al., *Plant Molec. Biol.* 26:657 (1994), cloned a gene from rice, designated as the OsMADS1 gene, that encodes a MADS-domain containing protein. Chung et al. showed that transgenic tobacco that express the OsMADS1 gene were characterized by early flowering and reduced apical dominance. Accordingly, early flowering transgenic poinsettia can be produced that express a foreign protein having the MADS box sequence. Suitable early flowering genes include the PLENA gene, the SQUAMOSA gene, the DEFICIENS A gene, the GLOBOSA gene, the APTELA1 gene, the APETALA3 gene, the AGAMOUS gene, the OsMADS24 gene, the OsMADS45 gene, and the OsMADS1 gene.

The present invention, thus generally described, will be understood more readily by reference to the following examples, which are provided by way of illustration and are not intended to be limiting of the present invention.

EXAMPLES

Table 5 summarizes results of studies described in detail below. In these studies the cultivars Angelika and Freedom were transformed with the DNA construct of interest using the methods described supra. More specifically, shoot tip or stem segments were incubated on callus induction medium for approximately 4 weeks, followed by culture on embryo induction medium for approximately 4 weeks. Embryogenic callus was transferred to liquid embryo induction medium and cultured with shaking for approximately 2 to 3 weeks. The cells were filtered through 2,000, 1,000 and 500 μm filters and the filtrate transferred to fresh liquid embryo induction medium. The cells were incubated form approximately 1 to 3 weeks and then filtered once again through 2,000, 1,000 and 500 μm filters. The filtrate was transferred to solid embryo induction medium and incubated for approximately 2 weeks. The developing embryos were transferred to maturation medium for approximately 6 weeks followed by culture on callus induction medium for approximately 3 weeks. The reddish epidermal callus was transferred to embryo induction medium for microparticle bombardment.

To obtain transformed cells, petri plates containing poinsettia callus were each bombarded once at a pressure of 1200 psi (helium) and a particle flight distance of 9 cm. Each plate was bombarded with 100 ng of cesium chloride-purified plasmid DNA (50 ng plasmid DNA containing the hph selectable marker gene cassette, and 50 ng plasmid DNA containing the horticultural gene of interest). One week after bombardment, the calli were transferred to an embryo induction medium containing 10 mg/liter hygromycin B for selection of Angelika transformants and 25 mg/liter hygromycin for selection of Freedom transformants. After two weeks, the calli were transferred from selection medium to a developmental medium. The transfer to developmental medium involved macerating the callus, then adding the macerated callus to liquid developmental medium in flasks which were placed on a gyratory shaker at 100 rpm overnight at 25° C. This callus suspension was then sieved to separate the callus from the embryos. The embryo suspension was then dripped onto solid developmental medium. The embryos remained on this medium for two weeks and were then transferred to a maturation medium where they remained for six weeks. At that time, somatic embryos were selected and transferred to germination medium. Approximately two weeks after germination, the small plantlets were transferred to a MS-based medium. All cultures were maintained at 25° C.±2° C. under lights for a 16 hour photoperiod.

TABLE 5

Detection of Transgene Products in Transgenic Poinsettia

| Promoter | Transgene | Detection Method |
| --- | --- | --- |
| E35S | tryptophan decarboxylase (TDC) | tryptamine (trm) accumulation |
| UBQ3 | TDC | trm accumulation |
| UBQ10 | TDC | trm accumulation |
| TEFA1 | TDC | trm accumulation |
| UBQ3 | snowdrop lectin | immunoassay |
| UBQ10 | snowdrop lectin | immunoassay |
| E35S | MSI-55 | in vitro anti-bacterial and anti-fungal assays |
| E35S | magainin 2 | in vitro anti-bacterial and anti-fungal assays |
| E3SS | MSI-99 | in vitro anti-bacterial and anti-fungal assays |
| E35S | D5-C | in vitro anti-bacterial and anti-fungal assays |
| 35S | MSI-55 | in vitro anti-bacterial and anti-fungal assays |
| UBQ3 | magainin 2 | in vitro anti-bacterial and anti-fungal assays |
| UBQ3 | D5-C | in vitro anti-bacterial and anti-fungal assays |
| UBQ3 | magainin 2-secreted peptide (Mag 2*S) | in vitro anti-bacterial and anti-fungal assays |
| UBQ3–UBQ10 | Mag 2*S/PGL-secreted peptide | in vitro anti-bacterial and anti-fungal assays |
| UBQ3–UBQ10 | PGL-secreted peptide/Mag2*S | in vitro anti-bacterial and anti-fungal assays |
| UBQ3 | Rs anti-fungal protein 2 | immunoassay and in vitro anti-fungal assay |

TABLE 5-continued

Detection of Transgene Products in Transgenic Poinsettia

| Promoter | Transgene | Detection Method |
|---|---|---|
| UBQ3 | endochitinase | chitinase assay |
| UBQ3 | endochitinase-secreted protein | chitinase assay |
| E35S | hygromycin phosphotransferase (hph) | detection of transcripts by PCR |
| UBQ3 | hph | PCR detection |
| TEFA1 | hph | PCR detection |
| UBQ10 | hph | PCR detection |
| E35S | OsMADS | whole plant screen |
| UBQ3 | phyA | whole plant screen |
| E35S | etr | whole plant screen |

Example 1

In Vitro Anti-Microbial Activity of Lytic Peptides

To test lytic peptides for antimicrobial activity, known amounts of pathogen were added to serial dilutions of peptide ranging from 0 to 256 µg/ml in individual wells of a 96-well microtiter plate. An equivalent volume of growth medium (LB broth for bacteria and potato dextrose broth for fungi) was added to each well and the plates incubated overnight at 25° C. with gentle shaking. The following day, wells were scored for the presence or absence of growth; the lowest concentration of peptide which inhibited all growth was recorded as the minimum inhibitory concentration (MIC) value. The phytopathogenic bacteria employed in the assays included *Pseudomonas syringae* and *Erwinia carotovora*. The phytopathogenic fungi included two isolates of *Phytophthora parasitica* (from petunia and vinca), *Fusarium solani*, *Fusarium graminearum*, *Thielaviopsis basicola*, *Botrytis cinerea* and *Rhizoctonia solani*.

As shown in Table 6, the bacteria were extremely sensitive (MIC <2 µg/ml) to the action of the lytic peptide analogs, MSI-99 and D5-C. In contrast, the natural peptides, magainin 2 and PGL alone were significantly less active against *Pseudomonas* and *Erwinia*. However, when combined in equimolar amounts, the magainin 2/PGL combination was even more potent than the peptide derivatives (MIC=0.5 µg/ml). In addition, each of the fungi assayed were sensitive to the action of at least one of the single lytic peptides. For example, both *Fusarium* species were extremely sensitive to treatment with the four single lytic peptides. In contrast, the two *Phytophthora* isolates were relatively resistant to the natural lytic peptides, with peptide analogs MSI-99 and D5-C showing the best anti-*Phytophthora* activity. *Thielaviopsis basicola*, *Botrytis cinerea* and *Rhizoctonia solani* exhibited intermediate levels of sensitivity to the various single peptides. Lytic peptide treatment of germinated and non-germinated spores produced essentially identical results. MSI-55 also displayed potent antibacterial and anti-fungal activity in vitro.

TABLE 6

Lytic Peptide Minimum Inhibitory Concentration (MIC) Values for Bacterial and Fungal Phytopathogens

| | Minimum Inhibitory Concentration (µg/ml) | | | | |
|---|---|---|---|---|---|
| Phytopathogen | Mag 2 | PGL | MSI-99 | D5-C | Mag 2/ PGL[b] |
| *Pseudomonas syringae* | 32 | >64 | 1 | NA | 2 |
| *Erwinia carotovora* | 32 | 32 | 1 | 2 | 0.5 |
| *Phytophthora parasitica* (vinca) | | | | | |
| non-germinated | >256 | >256 | 64 | 16 | >32 |
| germinated | >128 | >128 | 16–32 | 16–32 | >64 |
| *Phytophthora parasitica* (petunia) | | | | | |
| non-germinated | NA[c] | NA | NA | NA | NA |
| germinated | >128 | >128 | 8–16 | 16–32 | >64 |
| *Fusarium solani* | | | | | |
| non-germinated | 4 | 4 | 2 | 4 | 2 |
| germinated | 4–8 | 8–16 | 4 | 4 | 2 |
| *Fusarium graminearum* | | | | | |
| non-germinated | 4–8 | 4–8 | 4 | NA | 2 |
| germinated | NA | NA | NA | NA | NA |
| *Thielaviopsis basicola* | | | | | |
| non-germinated | 8 | 4–8 | 4 | 16 | 4 |
| germinated | 4 | 4 | 4 | 16 | 2 |
| *Botrytis cinerea* | | | | | |
| non-germinated | 8–16 | 4–8 | 8 | NA | 1–2 |
| germinated | 8 | 8 | 8 | NA | 1–2 |
| *Rhyzoctonia solani* R2 mycelial fragments | 16–32 | 16–32 | 16 | 32–64 | 2–4 |

[a]MIC: minimum peptide concentration required to inhibit all microbial growth after 24 hrs
[b]equimolar amounts of peptide added
[c]not assayed Overall, the most potent lytic peptide treatment was the magainin 2/PGL combination; all the fungi were extremely sensitive to this combination with the exception of *Phytophthora*. For example, the MIC value for *Rhizoctonia solani* with the combination was 2–4 µg/ml, nearly an order of magnitude less than the 16–32 µg/ml required with magainin 2 or PGL alone. A similar, though less dramatic difference was also observed with *Phytophthora*, *Botrytis* and *Fusarium*. Taken together, these results clearly demonstrate that broad spectrum antimicrobial activity was exhibited collectively by this group of lytic peptides. The synergy between magainin 2/PGL offers unique opportunities and new strategies for disease resistance. For example, if one peptide is secreted and the other is not, then upon pathogen attack the plasma membrane would be degraded and the synergy between secreted and non-secreted peptides would be activated against the pathogen.

Example 2

Production of Transgenic Poinsettia that Express Lytic Peptide Genes

The general strategy for constructing the lytic peptide genes was to chemically synthesize two partially overlapping single-strand oligonucleotides, allow the homologous regions to hybridize, and then complete the double strands in both directions by extension with Taq DNA polymerase. The oligonucleotide pair for each gene was designed with unique restriction sites located on each end of the gene (BamHI and SstI at the 5' and 3', ends, respectively) to allow directional cloning into plant expression vectors after restriction digestion. The general rules which were followed for gene construction included: (i) incorporation of the consensus sequence for translation initiation around the initiator codon to allow for optimal translation efficiency of the transcript; (ii) utilization of preferred dicot plant codons; and (iii) avoidance of long stretches of A and T residues which can destabilize RNA transcripts or inadvertently signal for polyA addition or intron splicing events. All clones were subjected to DNA sequence analysis to verify authenticity of the expected gene sequence. The nucleotide sequences of the lytic peptide genes are shown below.

Magainin 2:

ATG GGC ATC GGA AAG TTC CTT CAC AGT GCA AAG AAG

MET-GLY-ILE-GLY-LYS-PHE-LEU-HIS-SER-ALA-LYS-LYS

TTC GGA AAG GCC TTC GTG GGT GAG ATC ATG AAC AGT

PHE-GLY-LYS-ALA-PHE-VAL-GLY-GLU-ILE-MET-ASN-SER

TAA (SEQ ID NO:6)

--- (SEQ ID NO:7)

MSI-99:

ATG GGA ATC GGC AAG TTC CTC AAG AGC GCA AAG AAG

MET-GLY-ILE-GLY-LYS-PHE-LEU-LYS-SER-ALA-LYS-LYS

TTT GGC AAG GCC TTC GTG AAG ATC CTG AAC TCC

PHE-GLY-LYS-ALA-PHE-VAL-LYS-ILE-LEU-ASN-SER

TAA (SEQ ID NO:8)

--- (SEQ ID NO:9)

MSI-55:

ATG AAG ATC GCC GGA AAG ATA GCA AAG ATT GCG GGG

MET-LYS-ILE-ALA-GLY-LYS-ILE-ALA-LYS-ILE-ALA-GLY

AAA ATC GCG AAG ATC GCT GGC AAA ATC GCG

LYS-ILE-ALA-LYS-ILE-ALA-GLY-LYS-ILE-ALA

TAA (SEQ ID NO:10)

--- (SEQ ID NO:11)

D5-C:

ATG AAG AGG AAG CGT GCA GTT AAG AGG GTG GGA CGT

MET-LYS-ARG-LYS-ARG-ALA-VAL-LYS-ARG-VAL-GLY-ARG

CGA TTG AAG CTT GCA AGA AAG ATC GCA AGG CTC

ARG-LEU-LYS-LYS-LEU-ALA-ARG-LYS-ILE-ALA-ARG-LEU

GGT GTG GCT TTC TAA (SEQ ID NO:12)

GLY-VAL-ALA-PHE---- (SEQ ID NO:13)

Previous crop protection studies utilizing transgenes have shown that disease resistance levels can be influenced by the cellular location of the defense protein. For example, Melchers et al., *Plant Molec. Biol.* 21:583 (1993), demonstrated that optimal levels of resistance against infection by *Fusarium* were achieved by secretion of chitinase and β-1,3-glucanase into the intercellular space of transgenic tomato plants. These results are not surprising since pathogenesis-related proteins, such as chitinase and glucanase, induced after pathogenic attack, can be found in numerous cellular compartments, including the cytosol and the vacuole, as well as extracellularly. The lytic peptide genes first constructed as described above were designed to be translated and accumulate within the cytosol. However, it is possible that better protection against invading pathogens may be afforded by secretion of the lytic peptides into the intercellular space of the plant.

To transport the lytic peptides out of the plant cell, the signal peptide for the pea vicilin protein was fused in-frame (translationally) to the N-terminus of the lytic peptides. Previously, the 15-amino acid signal peptide of the pea vicilin protein had been demonstrated to direct efficient secretion of β-glucuronidase into the intercellular space of whole transgenic tobacco plants or into the liquid medium from transformed tobacco NT1 suspension cells. The vicilin signal peptide was very efficient in directing protein transport as little β-glucuronidase accumulated in the cytoplasm or remained sequestered in the endoplasmic reticulum. It was hypothesized that a protein secretion default pathway was the route of extracellular transport for the modified GUS enzyme.

An oligonucleotide which encoded the pea vicilin signal peptide was employed in polymerase chain reactions to create lytic peptides that are directed to the intercellular space. Since the signal peptide is cleaved during the secretory process, the final structure of the mature lytic peptides will be essentially no different than those peptides which lack this modification. The nucleotide sequences of the lytic peptide genes designed for secretion are presented below.

Magainin 2*S:

ATG CTT CTC GCT ATT GCC TTC TTG GCA TCA GTT TGC

MET-LEU-LEU-ALA-ILE-ALA-PHE-LEU-ALA-SER-VAL-CYS

GTG TCT TCC ATG GGC ATC GGA AAG TTC CTT CAC AGT

VAL-SER-SER-MET-GLY-ILE-GLY-LYS-PHE-LEU-HIS-SER

GCA AAG AAG TTC GGA AAG GCC TTC GTG GGT GAG ATC

ALA-LYS-LYS-PHE-GLY-LYS-ALA-PHE-VAL-GLY-GLU-ILE

ATG AAC AGT TAA (SEQ ID NO:14)

MET-ASN-SER---- (SEQ ID NO:15)

PGL*S:

ATG CTT CTC GCT ATT GCC TTC TTG GCA TCA GTT TGC

MET-LEU-LEU-ALA-ILE-ALA-PHE-LEU-ALA-SER-VAL-CYS

GTG TCT TCC GGA ATG GCC TCT AAG GCA GGT GCT ATC

VAL-SER-SER-GLY-MET-ALA-SER-LYS-ALA-GLY-ALA-ILE

GCC GGC AAA ATC GCG AAG GTG GCA TTG AAG GCC CTT

ALA-GLY-LYS-ILE-ALA-LYS-VAL-ALA-LEU-LYS-ALA-LEU

TAA (SEQ ID NO:16)

--- (SEQ ID NO:17)

MSI-99*S:

ATG CTT CTC GCT ATT GCC TTC TTG GCA TCA GTT TGC

MET-LEU-LEU-ALA-ILE-ALA-PHE-LEU-ALA-SER-VAL-CYS

GTG TCT TCC ATG GGA ATC GGC AAG TTC CTC AAG AGC

VAL-SER-SER-MET-GLY-ILE-GLY-LYS-PHE-LEU-LYS-SER

GCA AAG AAG TTT GGC AAG GCC TTC GTG AAG ATC CTG

ALA-LYS-LYS-PHE-GLY-LYS-ALA-PHE-VAL-LYS-ILE-LEU

AAC TCC TAA (SEQ ID NO:18)

ASN-SER---- (SEQ ID NO:19)

MSI-55*S:

ATG CTT CTC GCT ATT GCC TTC TTG GCA TCA GTT TGC

MET-LEU-LEU-ALA-ILE-ALA-PHE-LEU-ALA-SER-VAL-CYS

GTG TCT TCC AAG ATC GCC GGA AAG ATA GCA AAG

VAL-SER-SER-LYS-ILE-ALA-GLY-LYS-ILE-ALA-LYS

ATT GCG GGG AAA ATC GCG AAG ATC GCT GGC AAA

ILE-ALA-GLY-LYS-ILE-ALA-LYS-ILE-ALA-GLY-LYS

ATC GCG TAA (SEQ ID NO:20)

ILE-ALA---- (SEQ ID NO:21)

D5-C*S:

ATG CTT CTC GCT ATT GCC TTC TTG GCA TCA GTT TGC

MET-LEU-LEU-ALA-ILE-ALA-PHE-LEU-ALA-SER-VAL-CYS

GTG TCT TCC AAG AGG AAG CGT GCA GTT AAG AGG GTG

VAL-SER-SER-LYS-ARG-LYS-ARG-ALA-VAL-LYS-ARG-VAL

GGA CGT CGA TTG AAG AAG CTT GCA AGA AAG ATC GCA

GLY-ARG-ARG-LEU-LYS-LYS-LEU-ALA-ARG-LYS-ILE-ALA

AGG CTC GGT GTG GCT TTC TAA (SEQ ID NO:22)

ARG-LEU-GLY-VAL-ALA-PHE---- (SEQ ID NO:23)

The lytic peptide genes were placed under the transcriptional control of four possible promoters. The well-characterized native and enhanced versions of the CaMV 35S promoter were utilized. Also, the promoters of the UBQ3 and UBQ10 genes, members of the polyubiquitin gene family in *Arabidopsis thaliana*, were employed. The UBQ3 and UBQ10 promoters direct high levels of gene expression in transgenic poinsettia. All lytic peptide genes were flanked at their 3' ends by the nos 3' sequence containing the signal for polyA addition to the transcript. Tables 7 and 8 list relevant lytic peptide expression cassettes which have been created for introduction into poinsettia. All lytic peptide expression cassettes were constructed in pUC-derived cloning vectors.

TABLE 7

Plasmids for Cytosolic Localization of Lytic Peptides

| Lytic Peptide | Promoter | | | |
|---|---|---|---|---|
| | 35S | E35S | UBQ3 | UBQ10 |
| Magainin 2 | NA[a] | pSAN142 | pSAN163 | pSAN283 |
| PGL | NA | NA | NA | NA |
| MSI-55 | pSAN162 | pSAN141 | NA | NA |
| MSI-99 | NA | pSAN143 | pSAN164 | pSAN284 |
| D5-C | NA | pSAN144 | pSAN165 | NA |

[a]Not applicable

TABLE 8

Plasmids for Extracellular Localization of Lytic Peptides

| Lytic Peptide | Promoter | | |
|---|---|---|---|
| | E35S | UBQ3 | UBQ10 |
| Magainin 2 | pSAN146 | pSAN167 | pSAN284 |
| PGL | pSAN313 | pSAN315 | pSAN316 |
| MSI-55 | pSAN145 | pSAN166 | NA |
| MSI-99 | pSAN147 | pSAN168 | pSAN285 |
| D5-C | pSAN148 | pSAN169 | pSAN354 |
| Mag 2/PGL | NA | pSAN318–321 | pSAN318–321 |

[a]Not applicable

For construction of a vector which would express both magainin 2 and PGL, a total of four plasmids were assembled. To construct plasmids pSAN318 and pSAN319, the UBQ3::magainin 2 and UBQ10::PGL cassettes were combined into a single plasmid in two orientations (the opposite and same directions of transcription for pSAN318 and pSAN319, respectively). Similarly, the UBQ3::PGL and UBQ10::magainin 2 cassettes were situated on a single plasmid in two orientations (the opposite and same directions of transcription for pSAN320 and pSAN321, respectively) to generate plasmids pSAN320 and pSAN321.

An efficient and reliable in vitro anti-bacterial bioassay for detection of lytic peptide activity in transgenic poinsettia was developed. Briefly, cell-free extracts were prepared in 25 mM $KPO_4$, pH 5.5 buffer from tissue culture-maintained leaf tissue and $10^3$–$10^4$ *Pseudomonas syringae* bacteria in LB broth (5 µl) were added to 100 µg of leaf protein in a total volume of 50 µl. After a 2–2.5 hour incubation at room temperature to allow the peptides to interact with the bacteria, 1 ml of LB broth was added to the protein/bacteria mixture and incubated overnight at 28° C. The following day, the tubes were scored for bacterial growth; absence of growth indicates that the bacterial cells were killed by the action of the lytic peptides. An extract prepared from an untransformed plant and the same extract spiked with known amounts of purified lytic peptide were included as negative and positive controls, respectively, in all experiments. Typically, each transformant was subjected to this bioassay four times (two extracts prepared on separate days were assayed in duplicate on each day). Those transgenic lines which exhibited lytic peptide-mediated, anti-bacterial activity in three out of four bioassays were selected for advanced testing. A very useful feature of the assay is that the sensitivity of detection can be adjusted by manipulating the number of bacteria added to the tube. As can be observed in Table 9, typically, 20–50% of the transgenic lines subjected to the bioassay will test positive for lytic peptide activity. The actual percentage is highly dependent upon both the class of lytic peptide being expressed, and the lytic peptide expression cassette (i.e., promoter considerations).

TABLE 9

Transgenic Poinsettias Screened for Lytic Peptide-Mediated, Anti-Microbial Activity

| Variety | Plasmid | Antibacterial bioassay | | Botrytis Leaf Disk Assay | |
|---|---|---|---|---|---|
| | | Tested | Advanced | Tested | Advanced |
| Angelika | pSAN141 | 28 | 6 | 6 | 2 |
| | pSAN142 | 40 | 7 | 7 | 3 |
| | pSAN143 | 19 | 6 | 6 | 3 |
| | pSAN144 | 43 | 5 | 5 | 2 |
| | pSAN145 | 16 | 5 | 5 | 0 |
| | pSAN146 | 15 | 6 | 6 | 3 |
| | pSAN147 | 0 | 0 | 0 | 0 |
| | pSAN148 | 16 | 5 | 5 | 1 |
| | pSAN162 | 8 | 3 | 3 | 1 |
| | pSAN163 | 12 | 4 | 3 | 3 |
| | pSAN164 | 3 | 0 | 1 | 0 |
| | pSAN165 | 22 | 7 | 7 | 3 |
| | pSAN166 | 2 | 0 | 0 | 0 |
| | pSAN167 | 24 | 9 | 9 | 2 |
| | pSAN168 | 32 | 9 | 9 | 6 |
| | pSAN169 | 42 | 11 | 11 | 3 |
| | pSAN293 | 52[a] | 13 | 13 | 11 |
| | pSAN318 | 3 | 2 | 2 | 2 |
| | pSAN319 | 8 | 8 | 8 | 5 |
| | pSAN320 | 31 | 19 | 10 | 3 |
| Freedom | pSAN168 | 34 | 9 | NA[b] | NA |
| | pSAN293 | 63[a] | 17 | NA | NA |
| | pSAN319 | 90 | 52 | NA | NA |
| | pSAN321 | 84 | 42 | NA | NA |

[a]assayed by ELISA
[b]Not assayed

Following the anti-bacterial bioassay, candidate transgenic lines were selected for further analysis using an in vitro anti-fungal bioassay. Briefly, leaf discs from tissue culture-maintained transformed lines (and an untransformed control) were punched out with a cork borer and placed onto moistened Whatman 3M paper inside a sterile plastic bioassay dish. A freshly-prepared suspension of Botrytis cinerea spores was then pipetted onto the leaf disc surface. The humidity chamber was sealed and the leaf disks left at 20° C. to permit disease development. For the next 4–7 days, disease progression was monitored and recorded as percentage of leaf disks infected. Table 10 shows representative results obtained from this bioassay. As can be observed, a significant reduction in disease incidence was observed for transgenic poinsettia lines expressing a variety of lytic peptides. The level of Botrytis infection was often reduced as much as two to three-fold for many of the transgenic lines. This assay did not appear to detect any significant differences between transgenic lines which secreted the peptide versus those lines which retained the peptide in their cytosol.

TABLE 10

Reduced Incidence of Disease in Botrytis cinerea-inoculated Leaf Disks from Lytic Peptide-Expressing Poinsettias

| Plasmid | Peptide[b] | Disease Incidence[a] | | |
|---|---|---|---|---|
| pSAN142 | Mag 2 | 58 | 65 | 68 |
| pSAN143 | MSI-99 | 48 | 61 | 69 |
| pSAN144 | D5-C | 62 | 68 | 72 |
| pSAN146 | Mag 2*S | 51 | 51 | 59 |
| pSAN163 | Mag 2 | 66 | 68 | 70 |
| pSAN165 | D5-C | 42 | 60 | 67 |
| pSAN167 | Mag 2*S | 50 | 69 | 80 |
| pSAN168 | MSI-99*S | 31 | 40 | 52 |
| pSAN169 | D5-C*S | 30 | 38 | 70 |
| pSAN319 | Mag 2*S/PGL*S | 42 | 48 | 65 |
| pSAN319 | Mag 2*S/PGL*S | 47 | 66 | 80 |

[a]percent leaf discs infected relative to an untransformed control assigned a value of 100
[b]*S indicates secreted version of peptide Transgenic poinsettia lines that were positive for lytic peptide activity in both the in vitro anti-Pseudomonas and anti-Botrytis leaf disk assays were advance d to the next stages of disease screening. A second anti-Botrytis assay was developed to assess disease resistance on inoculated poinsettia cuttings. Briefly, shoots were harvested from greenhouse-grown transgenic plants and disinfected in a solution of 10% Clorox for five minutes, rinsed in water and then dipped in a spore suspension ($5 \times 10^5$ spores/ml). Inoculated shoots were incubated in a plastic bag for two days and then placed into wet oasis plugs under mist bed conditions to simulate commercial rooting practices. The disease incidence (percentage of cuttings infected) was recorded regularly and compared to inoculated, untransformed control shoots.

As can be observed in Table 11, the untransformed control shoots were sensitive to infection by Botrytis and quickly became heavily infected (disease ratings of 3–4). In contrast, a number of the lytic peptide-expressing lines showed greatly reduced symptoms after inoculation. Line 169-40, expressing D5-C*S, consistently showed disease ratings of about one or less in the three bioassays. Other transgenic lines which showed significantly reduced levels of Botrytis infection (all with a disease rating of about 2 or less) included 163-11 (Mag 2), 167-3 (Mag2*S), and 168-7 (MSI-99*S) and 168-24 (MSI-99*S). These results strongly support the conclusion that significant levels of resistance to Botrytis infection on poinsettia shoots are conferred by the lytic peptides.

TABLE 11

Disease Severity of Transgenic Angelika Cuttings Inoculated with Botrytis cinerea

| | Disease Index[a] (Experiment number) | | |
|---|---|---|---|
| Line | 1 | 2 | 3 |
| Control | 2.4 | 3.4 | 3.6 |
| 143-6. | 1.8 | 1.0 | 2.2 |
| 146-6 | 3.0 | 0.8 | 1.2 |
| 148-15. | 1.4 | 1.2 | 2.6 |
| 162-4 | 2.4 | 0 | 1.4 |
| 163-11. | 2.2 | 1.2 | 1.6 |
| 165-7. | 2.2 | 0.8 | 1.4 |
| 167-2 | 3.4 | 2.2 | 3.0 |
| 167-3. | 2.2 | 0.8 | 1.4 |
| 168-7. | 1.6 | 1.6 | 2.0 |
| 168-24. | 1.8 | 2.6 | 2.0 |

TABLE 11-continued

Disease Severity of Transgenic Angelika Cuttings
Inoculated with Botrytis cinerea

| | Disease Index[a] (Experiment number) | | |
|---|---|---|---|
| Line | 1 | 2 | 3 |
| 169-33. | 2.2 | 0.6 | 2.2 |
| 169-40. | 1.4 | 0.2 | 1.2 |

[a]mean disease index for five infected cuttings where:
0 = uninfected
1 = one older leaf infected or light infection on the young leaves
2 = young leaves falling off due to infection or severe infection on older leaves
3 = all leaves infected but <50% of leaf area infected
4 = all leaves severely infected and >50% of leaf area infected
5 = shoot collapsed
* = better tan control in all three experiments To assess whether increased levels of resistance to infection by a bacterial pathogen had been conferred by the lytic peptides, shoots were inoculated with *Erwinia carotovora* ss *carotovora*. Shoots from greenhouse-grown transgenic plants were trimmed to a length of three inches and all but three leaves were removed. A wound was made on the stem 1 inch from the stem tip with a sterile toothpick. The wound site was then inoculated with a pipette tip containing a 2 µl droplet of $10^4$ colony forming units (cfu's) of logarithmic phase ($OD_{590}$=0.000) *Erwinia carotovora*. Inoculated shoots were stuck into wet oasis plugs and then incubated in a moist chamber at 25° C. with a 16 hour photoperiod.

As can be observed in Table 12, untransformed control plants were extremely susceptible to infection by *Erwinia* as all reached disease ratings of 3–4 (4.0, 3.3, 4.0, 3.2, 3.2, 4.0) within five days. Once again, a number of lytic peptide-expressing lines demonstrated increased disease resistance properties after inoculation with *Erwinia*. In three assays, line 169-33 (D5-C*S) had disease ratings of about two or less (2.0, 1.0, 2.2). Another promising line included 165-7 (D5-C) with disease ratings of 3.0, 1.0, 2.7, 2.5 and 3.5.

As expected, a range of phenotypes were observed among the transgenics. Some transgenics were superior to the control plants, other transgenics were inferior, while some trangenics exhibited disease levels equal to controls and some were actually worse than the controls. It is not surprising that some transgenics are similar to the control because peptide expression levels must be above a certain threshold level to see any effect. This threshold level depends on the pathogen and the inoculation conditions. At very low levels of expression in planta, lytic peptides can actually increase disease severity in the transgenics. Accordingly, transgenic plants are carefully screened according to the methods described herein to identify plants that express the proper level of disease resistance. These plants are then propagated vegetatively to produced sufficient quantities of the disease resistant cultivar.

TABLE 12

Disease Severity of Lytic Peptide-Expressing Angelika
Five Days After Inoculation with Erwinia carotovora ss carotovora

| | Disease Index[a] (Experiment number) | | | | | |
|---|---|---|---|---|---|---|
| Line | 1 | 2 | 3 | 4 | 5 | 6 |
| Control | 4.0 | 3.3 | 4.0 | 3.2 | 3.2 | 4.0 |
| 143-6 | NA | 3.3 | NA | NA | 3.3 | NA |
| 146-6 | NA | 2.0 | NA | 1.7 | 4.0 | NA |

TABLE 12-continued

Disease Severity of Lytic Peptide-Expressing Angelika
Five Days After Inoculation with Erwinia carotovora ss carotovora

| | Disease Index[a] (Experiment number) | | | | | |
|---|---|---|---|---|---|---|
| Line | 1 | 2 | 3 | 4 | 5 | 6 |
| 148-15 | NA | 3.3 | 4.0 | NA | NA | NA |
| 163-11 | 4.0 | 3.3 | NA | 2.5 | 2.2 | 2.0 |
| 165-7* | 3.0 | 1.0 | NA | 2.7 | 2.5 | 3.5 |
| 167-2 | 4.0 | 3.0 | 2.0 | NA | 2.5 | 3.2 |
| 167-3* | NA | NA | 3.0 | NA | 1.8 | 3.5 |
| 168-7 | NA | NA | 4.0 | NA | 1.2 | NA |
| 168-24 | 2.3 | 3.6 | 3.6 | NA | 3.0 | 3.5 |
| 169-33* | 2.0 | 1.0 | NA | 2.2 | NA | NA |
| 169-40* | 3.0 | NA | NA | NA | 1.2 | NA |

[a]mean disease index for four infected cuttings where:
0 = uninfected
1 = inoculation site necrotic
2 = necrotic area spreading away from inoculation site
3 = necrotic area >20% of the stem
4 = stem necrotic and collapsed
* = better than control in test To more closely approximate commercial production conditions used for poinsettia, susceptibility to infection by *Erwinia* was repeated using shoots obtained from transgenic plants which had been grafted to restore the branching habit (see below). As shown in Table 13, shoots from untransformed control plants quickly became infected and reached disease ratings in the range of 3–4. Line 162-4 (MSI-55) exhibited significantly increased levels of *Erwinia* resistance as disease ratings were generally ≦2.5 in four of five bioassays (and as low as 1.2). Other interesting lines which showed reduced susceptibility to *Erwinia* included 167-24 (Mag 2*S) and 169-40 (D5-C*S). It should be noted that shoots from line 169-40 also showed quite impressive levels of resistance to infection by *Botrytis* after inoculation. This result indicates that lytic peptides can confer broad anti-bacterial and anti-fungal disease resistance properties within the same transgenic poinsettia plant.

TABLE 13

Disease Severity of Grafted, Lytic Peptide-Expressing
Angelika Poinsettias Five Days After Inoculation with
Erwinia carotovora ss carotovora

| | Disease Index[a] (Experiment number) | | | | |
|---|---|---|---|---|---|
| Line | 1 | 2 | 3 | 4 | 5 |
| Control | 3.0 | 3.8 | 3.2 | 3.5 | 2.8 |
| 162-4* | 2.2 | 2.5 | 3.0 | 2.2 | 1.2 |
| 165-2 | 3.5 | 3.5 | 2.5 | 2.5 | 3.2 |
| 165-7 | 3.2 | 4.0 | 2.5 | 2.7 | 3.2 |
| 167-2 | 3.7 | 4.0 | 3.5 | 3.2 | 3.5 |
| 167-3 | 3.0 | 3.0 | 3.5 | 3.2 | 3.0 |
| 167-24* | 2.5 | 3.5 | 2.0 | 2.5 | 2.5 |
| 168-7 | 4.0 | 4.0 | 4.0 | 3.5 | 3.0 |
| 168-24 | 4.0 | 3.0 | 2.5 | NA | 3.2 |
| 169-18 | 3.5 | 4.0 | 3.0 | 2.5 | 2.8 |
| 169-40* | 2.0 | 3.5 | 2.5 | 2.0 | 2.2 |

[a]mean disease index of four infected cuttings where:
0 = uninfected
1 = inoculation site necrotic
2 = necrotic area spreading away from inoculation site
3 = necrotic area >20% of the stem
4 = stem necrotic and collapsed
* = better than control in all 5 experiments Whole plants were screened for resistance to the powdery mildew pathogen. A total of 26 different Angelika lines transformed with a plasmid carrying either the gene for a single lytic peptide, or with a plasmid carrying both the magainin II and PGL lytic peptides, were screened in two different experiments.

In the first experiment 15 transgenic lines and a non-transgenic control were inoculated by placing them in close proximity to a heavily infected source plant. The inoculum source plants were removed after 7 days. At 15 days after initiation the mildew colonies were quantified on a specific leaf area using a dissecting microscope and lateral illumination of the leaves. The maximum number of conidia observed per catenulate chain was also recorded as a measure of colony age and productivity. At 20 days after initiation the colonies were again quantified on a specific leaf area without the aid of magnification. At 22 days after initiation the conidial crop from each plant line was harvested and quantified.

Colonies were plainly visible without magnification 2 weeks after initiation. The density of mildew colonies was significantly and substantially reduced from control levels on several transgenic lines; notably lines transformed with pSAN148, pSAN168, pSAN146, pSAN167 and pSAN168 as shown in Table 14. Likewise, the length of the latent period (generation time), as indirectly measured by the number of conidia produced per chain, was significantly increased above control levels on all transgenic lines as shown in Table 14.

TABLE 14

Severity of Powdery Mildew and Conidial Production

| | Colony Number[a] | | | Conidia per chain | | |
|---|---|---|---|---|---|---|
| Line | Mean | SE | CV % | Mean | SE | CV % |
| Control | 30.6 | 5.52 | 18 | 4.6 | 0.67 | 15 |
| 320-6 | 21.3 | 6.48 | 30 | 1.8 | 0.49 | 27 |
| 148-15 | 3.7 | 1.41 | 38 | 1.6 | 0.79 | 49 |
| 165-7 | 14.7 | 4.99 | 34 | 2.2 | 0.76 | 35 |
| 320-5 | 8.7 | 1.58 | 18 | 2.6 | 0.52 | 20 |
| 168-7 | 6.3 | 2.93 | 47 | 1.4 | 0.67 | 48 |
| 146-6 | 6.0 | 3.41 | 57 | 2.0 | 0.72 | 36 |
| 167-3 | 4.1 | 1.70 | 41 | 2.2 | 0.96 | 44 |
| 162-4 | 9.0 | 3.42 | 38 | 2.2 | 0.49 | 22 |
| 167-2 | 6.6 | 2.24 | 34 | 1.8 | 0.65 | 36 |
| 169-40 | 13.0 | 4.72 | 36 | 2.8 | 0.49 | 18 |
| 168-24 | 5.3 | 3.40 | 64 | 2.0 | 0.83 | 41 |
| 320-7 | no data | | | | | |
| 163-11 | no data | | | | | |
| 143-6 | no data | | | | | |
| 169-33 | no data | | | | | |

[a]Mean of three 6X fields of view per leaf.
SE = standard error of the mean.
CV = coefficient of variation
(ratio of standard error to mean expressed as %)

Resistance to powdery mildew continued to be expressed as reduced density of colonization when plants were again examined 20 days after initiation as shown in Table 15. The greatest reduction of disease was shown in plants transformed with pSAN 168, pSAN167 and pSAN146. Additionally, the total biomass of sporulating, mildew colonies was estimated by sampling airborne conidia downwind of whole plants. Very few conidia were trapped downwind of certain plants transformed with pSAN146, pSAN167 and pSAN168 as shown in Table 15. A plant selection transformed with pSAN168 had the lowest number of mildew colonies on day 20, but ranked seventh in reduction of sporulation as shown in Table 15. This selection also exhibited an 80% reduction in sporulation compared to the control.

TABLE 15

Severity of powdery mildew on transgenic and control poinsettia twenty days after initiation and production of conidia twenty two days after initiation.

| | Colonies[a] | | | Conidia per square cm[b] | | |
|---|---|---|---|---|---|---|
| Line | Mean | SE | CV % | Mean | SE | CV % |
| Control | 23.4 | 1.39 | 6 | 87.7 | 23.7 | 27 |
| 320-6 | 30.2 | 6.64 | 22 | 103.0 | 52.9 | 51 |
| 148-15 | 10.2 | 3.44 | 34 | 30.31 | 7.7 | 58 |
| 165-7 | 27.0 | 4.59 | 17 | 59.0 | 14.7 | 25 |
| 320-5 | 11.0 | 3.45 | 31 | 12.1 | 1.9 | 16 |
| 168-7 | 3.6 | 1.83 | 51 | 18.6 | 0.0 | 0 |
| 146-6 | 5.4 | 3.39 | 63 | 4.5 | 0.0 | 0 |
| 167-3 | 7.2 | 3.89 | 54 | 3.0 | 3.7 | 123 |
| 162-4 | 9.0 | 3.94 | 44 | 10.6 | 10.3 | 97 |
| 167-2 | 4.4 | 2.17 | 49 | 4.5 | 0.0 | 0 |
| 169-40 | 12.2 | 4.68 | 38 | 60.5 | 21.9 | 36 |
| 168-24 | 6.8 | 2.49 | 37 | 3.0 | 1.9 | 63 |
| 320-7 | 19.2 | 4.98 | 26 | 53.0 | 34.6 | 65 |
| 163-11 | 19.6 | 6.10 | 31 | 34.8 | 13.3 | 38 |
| 143-6 | 13.6 | 6.11 | 45 | 31.8 | 22.5 | 71 |
| 169-33 | 19.2 | 4.34 | 23 | 46.9 | 12.2 | 26 |

[a]Mean number of colonies per leaf segment defined by the midvein, two lateral veins, and the leaf margin. The number of colonies per segment was recorded on the top two fully expanded leaves on each of three plants per treatment. SE = standard error of the mean. CV = coefficient of variation (ratio of standard error to mean expressed as %).
[b]All infected leaves were removed from individual test plants and were beaten against the shroud of a rotary fan producing a wind speed of approximately 15 kph to dislodge conidia. An 18-mm square coverglass was placed 1 meter downwind to capture a sample of the total airborne spores from each plant. The coverglass was mounted in lactoglycerol and cotton-blue, examined at 160 X, and the number of conidia per 160 X transect was recorded. SE = standard error of the mean. CV = coefficient of variation (ratio of standard error to mean expressed as %).

In the second experiment involving analysis of resistance to powdery mildew, 12 different transgenic lines and the non-transgenic control were inoculated as described above. Thirteen days after initiation the number of colonies on the most severely infected leaf on each plant was recorded. A total of 2 transgenic lines transformed with pSAN319 and pSAN145 exhibited a significantly reduced density of mildew colonies compared to the non-transgenic control as shown in Table 16.

TABLE 16

Severity of powdery mildew on control and transgenic lines of poinsettia 13 days after initiation.
Colonies per infected leaf[a]

| Line | Mean | Standard error |
|---|---|---|
| Control | 31.8 | 9.76 |
| 319-1 | 53.5 | 20.28 |
| 319-3 | 35.3 | 13.54 |
| 148-5 | 27.8 | 12.95 |
| 318-3 | 85.3 | 49.45 |
| 319-4 | 21.3 | 7.73 |
| 146-4 | 37.8 | 24.84 |
| 320-5 | 31.5 | 10.24 |
| 145-15 | 18.0 | 5.74 |
| 318-1 | 48.8 | 30.05 |
| 319-7 | 5.3 | 1.69 |
| 145-16 | 33.5 | 6.27 |
| 319-5 | 42.0 | 21.22 |

[a]The most severely infected leaf on each plant was selected, and the total number of colonies per leaf was recorded.

Significant resistance to powdery mildew was expressed by 12 of the 26 transgenic lines tested. The resistance was expressed as (i) a reduction in the number of colonies, (ii) an increase in the duration of the latent period, and (iii) a reduction in the number of airborne spores downwind of infected plants.

Example 3

The Effect of Lytic Peptides on the Poinsettia Phytoplasma

Lee et al., *Nature Biotechnology* 15:178 (1997), recently demonstrated that the free-branching phenotype in commercial poinsettias is caused by the presence of a mycoplasma-like organism (MLO) or phytoplasma, as it has now been designated, within the phloem cells of the vascular system. Since MLO's are prokaryotic-like microorganisms, the potential for lytic peptide-mediated killing of the phytoplasma existed. To examine this possibility, transgenic poinsettia lines were grafted onto commercial, branching Angelika rootstock. Grafting was required since tissue culture conditions eradicate the phytoplasma from the poinsettia tissue. Fifteen transgenic Angelika lines, containing secreted or non-secreted single lytic peptides, were grafted to determine whether the lytic peptides affected the phytoplasma, and thus the branching habit. After a 68-day grafting period, cuttings of the transgenic (and non-transgenic control) lines were rooted, potted, grown for 3 weeks and pinched to 9 nodes. Six weeks after pinching, the length of the lateral branches at each node was measured.

As can be observed in Table 17, both branching and non-branching phenotypes were observed. Of the nine lines which were secreting the peptide into the extracellular space, only 2 of 9 (22%) were found to be non-branching. In contrast, 50% (3/6) of the lines which retain the peptide in their cytosol were observed to give a non-branching phenotype. Since the phytoplasma is thought to reside in the cytosol of the cell, the higher percentage of non-branching phenotypes in the lines which accumulate the peptide in the cytosol is consistent with the idea that exposure of the phytoplasma to the lytic peptides might have lethal consequences. Since the phytoplasma cannot be maintained outside the plant, no in vitro data existed a priori on the sensitivity of the phytoplasma to the peptides. However, these indicate that expression of lytic peptides in plants can be an effective manner in which to control diseases which are caused by infectious MLO agents. It should be noted that a branching phenotype was observed in 100% of the poinsettia lines (not transformed with lytic peptide genes) recovered after being subjected to the same transformation and grafting regime as the lytic peptide-expressing lines. This strongly argues that tissue culture conditions alone are not responsible for the non-branching phenotype observed in 33% (5/15) of the lytic peptide expressing lines examined. We believe this is the first example of genetically engineered resistance to any phytoplasma. Phytoplasmas cause important plant diseases such as lethal yellows in palm trees and aster yellows in vegetables such as carrots.

TABLE 17

The Effect of Lytic Peptides on Lateral Shoot Growth of Transgenic Poinsettias That Were Grafted to Restore the Branching Habit

| Line | Peptide | Avg. Shoot Length, nodes 1–3 (cm) | Avg. Shoot Length, nodes 4–9 (cm) | Phenotype |
|---|---|---|---|---|
| Nongrafted Control 1 | NA[a] | 16.0 | 0.0 | NB[b] |
| Nongrafted Control 2 | NA | 17.0 | 0.3 | NB |

TABLE 17-continued

The Effect of Lytic Peptides on Lateral Shoot Growth of Transgenic Poinsettias That Were Grafted to Restore the Branching Habit

| Line | Peptide | Avg. Shoot Length, nodes 1–3 (cm) | Avg. Shoot Length, nodes 4–9 (cm) | Phenotype |
|---|---|---|---|---|
| Grafted Control | NA | 10.6 | 9.8 | B[c] |
| Commercial Angelika 1 | NA | 15.0 | 14.2 | B |
| Commercial Angelika 2 | NA | 10.6 | 9.5 | B |
| 162-4 | MSI-55 | 14.3 | 17.2 | B |
| 162-7 | MSI-55 | 21.3 | 0.0 | NB |
| 163-6 | Mag 2 | 25.3 | 0.0 | NB |
| 163-11 | Mag 2 | 12.6 | 0.2 | NB |
| 165-2 | D5-C | 12.0 | 11.8 | B |
| 165-7 | D5-C | 12.6 | 12.6 | B |
| 167-2 | Mag 2*S | 8.6 | 11.2 | B |
| 167-3 | Mag 2*S | 10.3 | 6.0 | B |
| 167-24 | Mag 2*S | 12.6 | 13.3 | B |
| 168-7 | MSI-99*S | 9.3 | 5.0 | B |
| 168-22 | MSI-99*S | 16.3 | 0.1 | NB |
| 168-24 | MSI-99*S | 6.3 | 6.0 | B |
| 169-18 | D5-C*S | 12.3 | 12.8 | B |
| 169-33 | D5-C*S | 20.0 | 0.8 | NB |
| 169-40 | D5-C*S | 13.6 | 11.8 | B |

[a]Not applicable
[b]Not branching
[c]branching

Example 4

Production of Transgenic Poinsettia that Express the Defensin, Rs-AFP2

To confer fungal disease resistance properties in poinsettia, the Rs-AFP2 cDNA was transcriptionally fused to the *Arabidopsis* UBQ3 promoter (to create plasmid pSAN293) and introduced into poinsettia. Transgenic poinsettia lines were recovered and immunoassayed for the presence of the peptide. Briefly, total soluble protein was isolated from leaf tissue and coated onto the wells of 96-well microtiter plates for immunodetection by a direct ELISA method. An extract prepared from an untransformed control served as the negative control. The same control extract was spiked with known amounts of purified Rs-AFP2 peptide to act as a positive control and to serve as a standard for interpolation of the expression levels in the transgenic lines. As can be observed in Table 18, a number of transgenic lines were found to accumulate the peptide at levels ranging from 0.01% to 0.05% of the total soluble leaf protein. These levels are significant for a very small protein, about 5 kDa. For comparison to expression levels in tobacco, the range of protein accumulation varied from 0.04–0.2% of the total soluble leaf protein in homozygous $T_2$ tobacco lines expressing Rs-AFP2. No protein in the untransformed control sample reacted with the antiserum at detectable levels.

TABLE 18

RsAFP2 Accumulation in Poinsettia Leaf Tissue

| Line | [AFP2][a] | Disease Incidence[b] |
|---|---|---|
| Control | ND[c] | 100 |
| 293-16 | 0.02 | 94 |
| 293-18 | 0.02 | 62 |
| 293-19 | 0.05 | 57 |

TABLE 18-continued

RsAFP2 Accumulation in Poinsettia Leaf Tissue

| Line | [AFP2]$^a$ | Disease Incidence$^b$ |
|---|---|---|
| 293-20 | 0.02 | 48 |
| 293-21 | 0.03 | 61 |
| 293-23 | 0.02 | 44 |
| 293-25 | 0.02 | 71 |
| 293-29 | 0.02 | 48 |
| 293-31 | 0.03 | 76 |
| 293-33 | 0.04 | 85 |
| 293-37 | 0.02 | 65 |
| 293-42 | 0.01 | 76 |
| 293-47 | 0.01 | 76 |

$^a$percent of total soluble leaf protein
$^b$percent leaf disks infected relative to an untransformed control
$^c$not detected Transgenic lines expressing Rs-AFP2 peptide were selected for further analysis using the anti-*Botrytis* leaf disk assay. Three transgenic lines, 293-20, 293-23, and 293-29 exhibited 2 to 3-fold reduced incidence of *Botrytis* infection compared to an untransformed control. Other transgenic lines showed lesser, but reproducible levels of protection against *Botrytis* infection. These results are very similar to those which were found for the transgenic lines expressing other lytic peptides such as magainin 2, MSI-99 and D5-C. See Table 18.

Example 5

Expression of Tryptophan Decarboxylase in Transgenic Poinsettia

To assess whether tryptamine was acutely toxic to whitefly, artificial feeding studies were conducted in which whiteflies were fed artificial diets supplemented with a range of tryptamine concentrations. Tryptamine concentrations as low as 50–100 μg/ml proved quite toxic to *Bemisia*.

To determine the effect of increasing TDC activity in poinsettia, a series of TDC expression cassettes were constructed for expression in poinsettia. See Table 19. The TDC cDNA was fused to the enhanced version of the CaMV 35S promoter and the *Arabidopsis* UBQ3 promoter. In addition, the *Arabidopsis* UBQ10 and TEFA 1 promoters were employed to direct TDC expression. These latter two promoters have been demonstrated to direct very high levels of transgene expression in the phloem of transgenic petunias. This is particularly significant since the phloem is the site of feeding for *Bemisia* on poinsettia.

TABLE 19

Plasmids for TDC Expression in Poinsettia

| Plasmid | Promoter |
|---|---|
| pSAN215 | E35S |
| pSAN247/248$^a$ | UBQ3 |
| pSAN264/265$^a$ | TEFA 1 |
| pSAN291 | UBQ10 |

$^a$the plasmid pair can be considered equivalent

Transgenic TDC-expressing poinsettia lines were recovered and analyzed by HPLC for their tryptamine content. See Table 20. Leaves from untransformed poinsettia accumulated only about 5 μg/gram fresh weight (gfw) tryptamine while the leaves from transgenic lines accumulated up to 40–50 μg/gfw leaf tissue. The tryptamine levels in poinsettia leaves were similar to the levels found in TDC expressing canola leaves (up to 50 μg/gfw) and potato leaves (up to 100 μg/gfw), but well below those found in tobacco (in excess of 1000 μg/gfw).

TABLE 20

Tryptamine Accumulation in the Leaves and Phloem of TDC-Expressing Poinsettias

| | [Tryptamine] (μg/gfw)$^a$ | |
|---|---|---|
| Line | Leaf | Phloem |
| Control | 5 | 4 |
| 215-1 | 31 | NA$^b$ |
| 215-4 | 12 | NA |
| 247-16 | 41 | NA |
| 247-17 | 91 | NA |
| 247-23 | 46 | NA |
| 247-33 | 41 | NA |
| 247-34 | 41 | NA |
| 247-36 | 42 | NA |
| 247-37 | 43 | NA |
| 247-39 | 41 | NA |
| 247-42 | 39 | NA |
| 265-3 | 29 | 6 |
| 265-4 | 49 | 9 |
| 265-14 | 37 | 9 |
| 291-7 | 46 | 4 |
| 291-32 | 72 | 4 |
| 291-33 | 24 | NA |

$^a$μg tryptamine per gram fresh weight tissue
$^b$not assayed

Despite relatively modest tryptamine levels in poinsettia leaf compared to tobacco leaf, tryptamine content in the phloem, the site of feeding for *Bemisia*, remained unknown. Thomas et al., *Plant Physiol.* 109: 717 (1995) had previously noted that tobacco lines with low tryptamine levels in the phloem still exhibited anti-whitefly properties. Phloem exudates from an untransformed control and selected TDC-expressing poinsettia lines were collected and analyzed for their tryptamine content. As shown in Table 20, the control line and two pSAN291 lines (UBQ10::TDC) contained 4 μg/gfw tryptamine. However, the three pSAN265 lines (TEFA 1::TDC) showed slightly elevated tryptamine levels in the phloem exudate. These tryptamine levels in the phloem are very similar to those reported by Thomas et al. (1995) for transgenic tobacco. Whitefly larval/pupal development and adult emergence were monitored on the tryptamine accumulating and untransformed control poinsettias. As can be observed in FIG. 1, all three transgenic lines transformed with pSAN264 showed decreased rates of adult emergence at 30 days relative to the control, indicating developmental delay. At 40 days, when adult emergence was complete, the three transgenic lines showed reduced levels of emergence compared to the control. Taken together, the data obtained at 30 and 40 days are consistent as they suggest deleterious effects exerted by tryptamine on *Bemisia* during larval/pupal development on poinsettia.

Example 6

Production of Transgenic Poinsettia that Express GNA Lectin

The cDNA for the GNA lectin, which was cloned by Van Damme et al., *Eur. J. Biochem.* 202:23 (1991), was fused to the *Arabidopsis* UBQ3 (pSAN260/261), UBQ10 (pSAN296/297) and TEFA 1 (pSAN262/263) promoters (each pair of plasmids within parentheses can be considered equivalent) for expression in poinsettia. See Table 21.

TABLE 21

Plasmids for GNA Expression in Poinsettia

| Plasmid | Promoter |
| --- | --- |
| pSAN260/261 | UBQ3 |
| pSAN262/263 | TEFA 1 |
| pSAN296/297 | UBQ10 |

Transgenic lines which were bombarded with the GNA transgenes were recovered for analysis. Total soluble protein was isolated from poinsettia leaf tissue and coated onto the wells of a 96-well microtiter plate for immunodetection by a direct ELISA method. An untransformed control served as the negative control whereas this same extract spiked with known amounts of purified GNA lectin acted as the positive control and the standard by which the protein levels in the transgenic lines were calculated. As can be observed in Table 22, a number of transgenic lines accumulated GNA lectin.

Table 23 summarizes the progress achieved in the recovery and evaluation of transgenic poinsettia lines expressing two different anti-insect genes.

TABLE 22

GNA Accumulation in Transgenic Poinsettia

| Line | [GNA][a] |
| --- | --- |
| Control | ND[b] |
| 260-10 | 0.03 |
| 260-29 | 0.02 |
| 260-33 | 0.04 |
| 260-40 | 0.02 |
| 260-55 | 0.01 |
| 261-7 | 0.01 |
| 261-18 | 0.01 |
| 261-20 | 0.01 |
| 262-1 | 0.02 |
| 296-4 | 0.04 |
| 296-6 | 0.02 |
| 296-9 | 0.01 |
| 296-11 | 0.01 |

[a]percent of total soluble leaf protein
[b]not detected

TABLE 23

Transgenic Angelika Poinsettia Lines Screened for the Expression of Anti-Insect Transgenes

| Anti-Insect Gene | Plasmid | Number of Lines Tested | Number of Lines Expressing |
| --- | --- | --- | --- |
| TDC | pSAN247 | 25 | 4 |
|  | pSAN248 | 16 | 6 |
|  | pSAN264 | 22 | 0 |
|  | pSAN265 | 16 | 16 |
|  | pSAN291 | 42 | 2 |
| GNA | pSAN260 | 57 | 6 |
|  | pSAN261 | 23 | 3 |
|  | pSAN262 | 8 | 1 |
|  | pSAN263 | 6 | 0 |
|  | pSAN296 | 17 | 6 |

Example 7

Production of Ethylene-insensitive Poinsettia

Figure 2:
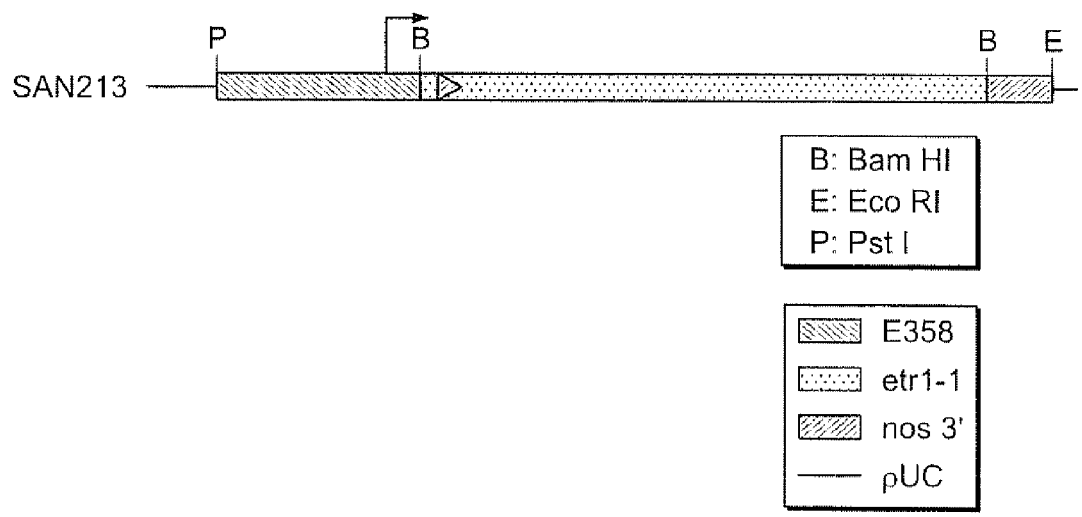
FIG. 2 illustrates plasmid pSAN213.

To genetically engineer ethylene-insensitive poinsettias, an etr1-1 cDNA was first generated by replacing a restriction fragment from the wild-type etr1 cDNA with the homologous fragment isolated from the genomic clone of the etr1-1 gene. The *Arabidopsis* etr-1 gene was described in Chang et al., *Science* 262: 539 (1993). The mutant etr1-1 cDNA was then placed under the transcriptional control of the enhanced version of the CAMV 35S promoter to create plasmid pSAN213. A map of plasmid pSAN213 is shown in FIG. 2. Plasmid pSAN213 was then bombarded into epidermal callus from the cultivar Freedom and transformed plants were covered according to the methods described supra.

To test for ethylene sensitivity, untransformed and transgenic poinsettia plants were exposed to 15 µl/liter ethylene for 24 hours to induce epinasty. In general, the youngest leaves of the plants showed the most dramatic signs of epinasty, and thus were the most useful for assessing the relative sensitivities to ethylene. In ethylene-sensitive control plants, the youngest leaves and petioles turned downward so sharply that the leaves were tight against the stem of the plant. Older leaves exhibited an overall droopy appearance. However, a significant number of the pSAN213-transformed poinsettias showed markedly reduced symptoms of epinasty. In these plants, the youngest leaves turned downward to a lesser extent and the older leaves remained more upright. Using this assay, we have found that 6 of 17 transgenic Freedom lines examined have shown reduced signs of epinasty.

A secondary phenotype in the ethylene-treated poinsettias has been noted which provides an extremely useful visible marker of ethylene-induced epinasty. Within 15 to 30 minutes after removing the poinsettia plants from the ethylene chamber, those lines which had already been rated as ethylene-sensitive began to show severe signs of wilting. The leaves lost turgor, curled, and drooped precipitously. This effect was transient as generally within 2–4 hours the plants began to regain turgor. However, we have observed that some leaves never recover turgor and these leaves die. In contrast, the ethylene-insensitive lines showed dramatically reduced symptoms, if any at all. To demonstrate that this phenotype was ethylene-related, poinsettia plants were sprayed to the point of runoff with a 4 mM solution of silver thiosulfate (STS), an antagonist of ethylene action. At 18 hrs after STS treatment, the STS-treated poinsettias were exposed to ethylene for 24 hours. After the ethylene treatment, the STS-treated plants showed little, if any, signs of epinasty or wilting. This observation indicated that the wilting was directly related to the action of ethylene, and could be considered a diagnostic marker for poinsettia plants which are ethylene sensitive.

Example 8

Genetic Engineering of Modified Plant Habit in Poinsettia Plants

The OsMADS1 gene from rice, when over-expressed in tobacco, causes early flowering and more compact plant habit and photoperiod insensitivity. Chung et al., *Plant Mol. Biol.* 26: 657–665 (1994). The phyA gene has also been shown to confer more compact habit and phytochrome is known to be involved in photoperiod regulation. McCormac et al., *Planta* 185: 162–170 (1991). Accordingly, the OsMADS1 and phyA genes are known.

The OsMADS1 and phyA genes were sub-cloned into expression vectors and operably linked to the E35S and UBQ3 promoters, respectively using methods well-known in the art. These plasmids were transformed into poinsettia cultivar Angelica according to the methods described supra.

A total of 10 transgenic plants carrying the phyA gene and 1 transgenic plant carrying the OsMADS1 gene were recovered. Plants were grown in the greenhouse to observe their phenotype compared to wild type control plants.

Under greenhouse conditions 3 poinsettia plants transformed with the phyA gene, and the plant transformed with the OsMADS1 gene differed from the control in that these transgenic*** plants had shorter internodes. In the absence of any controlled artificial photoperiod, in the fall of the year with approximately 14 hour days, these same transgenic plants began to flower (showing red bracts). The control plants did not flower under these conditions. Normally poinsettia plants do not begin to flower unless the day length is 12 hours or less.

In order to further evaluate the effect the photoperiod on flowering in the transgenic plants, they were exposed to artificial daylight for 16 hrs. All of the plants treated with longer periods of daylight reverted to vegetative growth. Several months later the plants which had begun to flower early began to show a greater tendency to branch than the controls. Early flowering, shorter nodes, and more free branching are all desired features in poinsettia cultivars.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patent applications mentioned in this specification are indicative of the level of skill of those in the art to which the invention pertains. All publications and patent applications are herein incorporated by reference to the same extent as if each individual publication or patent application were specifically and individually indicated to be incorporated by reference in its entirety.

What is claimed is:

1. A transgenic poinsettia plant comprising at least one expression vector, wherein said expression vector comprises at least one foreign gene, and wherein said transgenic poinsettia plant expresses said foreign gene.

2. The transgenic poinsettia plant of claim 1, wherein said expression vector further comprises a promoter, wherein said promoter is selected from the group consisting of Cauliflower Mosaic Virus (CaMV) 35S promoter, the enhanced 35S promoter, the UBQ3 promoter, the UBQ10 promoter, the UBQ11 promoter, the UBQ14 promoter, the TEFA 1 promoter, the rolC promoter, and the Commelina Yellow Mottle Virus promoter, wherein the expression of said foreign gene is under the control of said promoter.

3. The transgenic poinsettia plant of claim 2, wherein said promoter is selected from the group consisting of the CaMV 35S promoter, the enhanced 35S promoter, the UBQ3 promoter, and the UBQ10 promoter.

4. The transgenic poinsettia plant of claim 1, wherein the expression of said foreign gene confers resistance to disease caused by an organism selected from the group consisting of virus, bacterium, and fungus.

5. The transgenic poinsettia plant of claim 4, wherein said foreign gene disrupts the function of said virus, and wherein said virus-disrupting gene is selected from the group consisting of genes encoding viral coat protein, 2'–5' oligonucleotide synthetase, viral genome antisense RNA, and pokeweed B81 antiviral protein.

6. The transgenic poinsettia plant of claim 1, wherein said foreign gene confers resistance to an insect, and wherein said insect resistance gene encodes a protein selected from the group consisting of tryptophan decarboxylase, lectin, and *Bacillus thuringiensis* toxin.

7. The transgenic poinsettia plant of claim 6 wherein said lectin is *Galanthus nivalis* lectin.

8. The transgenic poinsettia plant of claim 4, wherein said foreign gene confers resistance to a bacterium or a fungus and encodes a polypeptide selected from the group consisting of chitinase, a β-1,3-glucanase, ribosome-inactivating protein, lytic peptide, and plant defensin.

9. The transgenic poinsettia plant of claim 8, wherein said plant defensin is radish seed Rs-AFP2.

10. The transgenic poinsettia plant of claim 8, wherein said lytic peptide is selected from the group consisting of a magainin, PGLa, PGL, xenopsin, caerulein, cecropin, MSI-99, MSI-55, and D5-C.

11. The transgenic poinsettia plant of claim 1, wherein said foreign gene is operatively linked with a DNA molecule encoding pea vicilin signal peptide.

12. The transgenic poinsettia plant of claim 10, wherein said magainin in magainin 1 or magainin 2.

13. The transgenic poinsettia plant of claim 1, wherein said transgenic poinsettia comprises an expression vector that further comprises a second foreign gene.

14. The transgenic poinsettia plant of claim 13, wherein said foreign gene encodes chitinase, and wherein said second foreign gene encodes β-1,3-glucanase.

15. The transgenic poinsettia plant of claim 13, wherein said foreign gene encodes magainin 2, and wherein said second foreign gene encodes PGLa or PGL.

16. The transgenic poinsettia plant of claim 1, wherein the expression of said foreign gene confers insensitivity to ethylene, and wherein said foreign gene encodes a mutated ethylene receptor.

17. The transgenic poinsettia plant of claim 16, wherein said mutated ethylene receptor gene is the *Arabidopsis* etr-1 gene or a tomato NR gene.

18. The transgenic poinsettia plant of claim 1, wherein said foreign gene is the *Vitreoscilla* hemoglobin gene.

19. The transgenic poinsettia plant of claim 1, wherein said foreign gene is an isopentyenyl transferase gene, wherein the expression of said isopentynyl transferase gene is under the control of a promoter of a senescence-associated gene.

20. The transgenic poinsettia plant of claim 19, wherein said promoter is the *Arabidopsis* SAG12 gene promoter.

21. The transgenic poinsettia plant of claim 1, wherein said foreign gene encodes a polypeptide having a MADS box domain.

22. The transgenic poinsettia plant of claim 21, wherein said second foreign gene is selected from the group consisting of the PLENA gene, the SQUAMOSA gene, the DEFICIENS A gene, the GLOBOSA gene, the APTELA1 gene, the APETALA2 gene, the AGAMOUS gene, the OsMADS24 gene, the OsMADS45 gene, and the OsMADS1 gene.

23. The transgenic poinsettia plant of claim 1, wherein said foreign gene encodes a protein that modifies plant habit.

24. The transgenic poinsettia plant of claim 23, wherein said gene is the OsMADS1 or phyA gene.

25. The transgenic poinsettia plant of claim 1, wherein said plant is fertile.

26. The transgenic poinsettia plant of claim 1, wherein the expression of said second foreign gene confers resistance to an insect.

* * * * *